US006153386A

United States Patent [19]
Lalouel et al.

[11] Patent Number: 6,153,386
[45] Date of Patent: Nov. 28, 2000

[54] METHOD TO DETERMINE PREDISPOSITION TO HYPERTENSION

[75] Inventors: Jean-Marc Lalouel, Salt Lake City, Utah; Xavier Jeunemaitre, Paris, France

[73] Assignee: University of Utah Research Foundation, Salt Lake City, Utah

[21] Appl. No.: 09/106,216

[22] Filed: Jun. 29, 1998

Related U.S. Application Data

[63] Continuation-in-part of application No. 09/092,988, Jun. 8, 1998, which is a continuation of application No. 08/319,545, Oct. 7, 1994, Pat. No. 5,763,168, which is a continuation-in-part of application No. 07/952,442, Sep. 30, 1992, Pat. No. 5,374,525.

[51] Int. Cl.$^7$ .............................. C12Q 1/68; C12P 19/34; C07H 21/04
[52] U.S. Cl. .......................... 435/6; 435/91.2; 536/23.5; 536/24.31; 536/24.33
[58] Field of Search ..................... 435/6, 91.2; 536/23.5, 536/24.31, 24.33

[56] References Cited

U.S. PATENT DOCUMENTS

| | | | |
|---|---|---|---|
| 5,374,525 | 12/1994 | Lalouel et al. | 435/6 |
| 5,589,584 | 12/1996 | Lalouel et al. | 536/24.31 |
| 5,763,168 | 6/1998 | Lalouel et al. | 435/6 |

OTHER PUBLICATIONS

Ishigami et al. Hypertension. 30:1325–1330, Dec. 1997.

Arngrimsson, R. et. al. (1993). "Angiotensinogen: a Candidate Gene Involved in Preeclampsia." Nature Genetics 4:114–115.

Bachmann, J., et. al. (1991). "Sexual Dimorphism of Blood Pressure:Possible Role of the Renin Angiotensin System." J. Steroid Biochem. Mol. Biol. 40:511–515.

Bennett, C.L. et. al. (1993). "Cross–sectional Analysis of Met$^{235}$ → Thr Variant of Angiotensinogen Gene in Severe, Familial Hypertension." Biochem. Biophys. Res. Commun. 197:833–839.

Caulfield, M., et al. (1996). "Angiotensinogen in Human Essential Hypertension." Hypertension 28:1123–1125.

Caulfield, et. al. (1994). "Linkage of the Angiotensinogen Gene to Essential Hypertension." J. Clin. Invest. 96:687–692 (1995).

Fukamizu, A., et. al. (1990). "Structure and Expression of the Human Angiotensinogen Gene." J. Biol. Chem. 265:7576–7582.

Gaillard, I. et. al. (1989). "Structure of Human Angiotensinogen Gene." DNA 8:87–99.

Grim, et. al. (1994). "The Angiotensinogen Gene MT235 is not Associated with Blood Pressure in Blacks on Dominica." Abstract 49 from an unknown source.

Hata, A. et. al. (1995). "Role of Angiotensinogen in the Genetics of Essential Hypertension." Life Sci. 57:2385–2395.

Hata, A. et. al. (1994). "Angiotensinogen as a Risk Factor for Essential Hypertension in Japan." J. Clin. Invest. 93:1285–1287.

Hegele, R.A., et. al. (1994). "A Polymorphism of the Angiotensinogen Gene Associated Gene Associated with Variation in Blood Pressure in a Genetic Isolate." Circulation 90:2207–2212.

Hilbert, P., et. al. (1991). "Chromosomal Mapping of the Genetic Loci Associated with Blood Pressure Regulation in Hereditary Hypertensive Rats." Nature 353:521–528.

Hixson, J.E., et. al. (1995). "Detection and Characterization of New Mutations in the Human Angiotensinogen Gene." Hum. Genet. 96:110–112.

Inoue, I., et. al. (1995). "A Mutation of Angiotensinogen in a Patient with Preeclampsia Leads to Altered Kinetics of Renin–Angiotensin System." J. Biol. Chem. 270:11430–11436.

Inoue, I., et. al. (1997). "A Nucleotide Substitution in the Promoter of Human Angiotensinogen is Associated with Essential Hypertension and Affects Basal Transcription in vitro." J. Clin. Invest. 99:1786–1797.

Iwai, N., et. al. (1995). "Angiotensinogen Gene and Blood Pressure in the Japanese Population." Hypertension 25(pt2):688–693.

Jeunemaitre, X., et. al. (1997). "Haplotypes of Angiotensinogen in Essential Hypertension." Am. J. Hum. Genet. 60:1448–1460.

Jeunemaitre, X., et. al. (1993). "M235T variant of the Human Angiotensinogen Gene in Unselected Hypertensive Patients." J. Hypertension 11(supp. 5):S80–S81.

Jeunemaitre, X., et. al. (1992). "Molecular Basis of Human Hypertension: Role of Angiotensinogen." Cell 71:169–80.

Jeunemaitre, X., et. al. (1992). "Absence of Linkage Between the Angiotensin Converting Enzyme Locus and Human Essential Hypertension." Nature Genetics 1:72–75.

Jeunemaitre, X., et. al. (1992). "Sib Pair Linkage Analysis of Renin Gene Haplotypes in Human Essential Hypertension." Human Genetics 88:301–306.

Kim, H.–S., et. al. (1995). "Genetic Control of Blood Pressure and the Angiotensinogen Locus" Proc. Natl. Acad. Sci. USA 92:2735–2739.

Kotelevisev, Y.V., et. al. (1991). "Dinucleotide Repeat Polymorphism in the Human Angiotensin Gene." Nucl. Acids Res. 19:6978.

Lu, et. al. (1994). "Cross–Sectional Analysis of Angiotensinogen Genotypes and Blood Pressure in Mexican Americans." Abstract 51 from unknown source.

(List continued on next page.)

*Primary Examiner*—Carla J. Myers
*Attorney, Agent, or Firm*—Rothwell, Figg, Ernst & Kurz, P.C.

[57] ABSTRACT

The association of the molecular variant A-20C of the angiotensinogen gene with the prognosis of human hypertension as determined by the G-6A molecular variant is disclosed. The determination of this association enables the screening of persons to identify the severity of hypertension or the severity of the risk of a predisposition to high blood pressure.

18 Claims, No Drawings

OTHER PUBLICATIONS

Morgan, et. al. (1996). "DNA Polymorphisms and Linkage Disequilibrium in the Angiotensinogen Gene." Human Genetics 98:194–98.

Ptacek, L.J., et. al. (1991). "Analysis in a Large Hyperkalemic Periodic Paralysis Pedigree Supports Tight Linkage to a Sodium Channel Locus." Am. J. Hum. Genet. 49:378–382.

Rotimi, C. et. al. (1994). "Angiotensinogen Gene in Human Hypertension." Hypertension 24:591–594.

Rutledge, D.R. et. al. (1994). "Analysis of Two Variants of the Angiotensinogen Gene in Essential Hypertensive African–Americans." Am. J. Hypertension 7:651–654.

Schmidt, S., et. al. (1995). "Association of M235T Variant of the Angiotensinogen Gene with Familial Hypertension of Early Onset." Nephrol. Dial. Transplant 10:1145–1148.

Soubier, F. et. al. (1990). "Similar Frequencies of Renin Gene Restriction Fragment Length Polymorphisms in Hypertensive and Normotensive Subjects." Hypertension 16:712–17.

Watt, G.C., et. al. (1992). "Abnormalities of Glucocorticoid Metabolism and the Renin–Angiotensin System: A Four Corners Approach to the Identification of Genetic Determinants of Blood Pressure." J. Hypertens. 10:473–482.

Yanai, K.Y., et. al. (1997). "Molecular Variation of the Human Angiotensinogen Core Promoter Element Located between the TATA Box and Transcription Initiation Site Affects Its Transcriptional Activity." J. Biol. Chem. 272:30558–30562.

Yanai, K.Y., et. al. (1996). "A cis–acting DNA Element Located between TATA Box and Transcription Initiation Site Is Critical in Response to Regulatory Sequences in Human Angiotensinogen Gene." J. Biol. Chem. 271:15981–15986.

Morgan, L. et al. (1996). DNA polymorphisms and linkage disequilibrium in the angiotensinogen gene. Hum. Genet. 98:194–198.

Ishigami, T. et al. (1997). Essential hypertension and 5'upstream core promoter region of human angiotensinogen gene. Biosis Abstract No. 1262178.

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

ACCATTTGCA ATTTGTACAG C                             21

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single (D) TOPOLOGY: linear (ii) MOLECULE TYPE: other nucleic acid
        (A) DESCRIPTION: /desc = "primer"

(xi) SEQUENCE DESCRIPTION: SEQ ID NO:2:

GCCCGCTCAT GGGATGTG                                                          18

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

AAGACTCTCC CCTGCCCCTC T                                                      21

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:4:

GAAGTCTTAG TGATCGATGC AG                                                     22

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

AGAGGTCCCA GCGTGAGTGT                                                        20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:6:

AGACCAGAAG GAGCTGAGGG                                                        20

(2) INFORMATION FOR SEQ ID NO:7:

(i) SEQUENCE CHARACTERISTICS:
        (A) LENGTH: 23 base pairs
        (B) TYPE: nucleic acid

```
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

GTTAATAACC ACCTTTCACC CTT                                          23

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:8:

GCAGGTATGA AGGTGGGGTC                                              20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

AGGCCAATGC CGGGAAGCCC                                              20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

ATCAGCCCTG CCCTGGGCCA                                              20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

GATGCGCACA AGGTCCTGTC                                              20

(2) INFORMATION FOR SEQ ID NO:12:

(i) SEQUENCE CHARACTERISTICS:
        (A) LENGTH: 20 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

GCCAGCAGAG AGGTTTGCCT                                              20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

TCCCTCCCTG TCTCCTGTCT                                              20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:14:

TCAGGAGAGT GTGGCTCCCA                                              20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:15:

TGGAGCCTTC CTAACTGTGC                                              20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:16:

AGACACAGGC TCACACATAC                                              20

(2) INFORMATION FOR SEQ ID NO:17:

(i) SEQUENCE CHARACTERISTICS:

(A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:17:

GTCACCCATG CGCCCTCAGA                                                   20

(2) INFORMATION FOR SEQ ID NO:18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:18:

GTGTTCTGGG GCCCTGGCCT                                                   20

(2) INFORMATION FOR SEQ ID NO:19:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:19:

ACTGCACTCC AGCCTCGGAG                                                   20

(2) INFORMATION FOR SEQ ID NO:20:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:20:

AGAAAAGTCC TTTCTCCAGA GCA                                               23

(2) INFORMATION FOR SEQ ID NO:21:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:21:

GGTCAGGATA GATCTCAGCT                                                   20

(2) INFORMATION FOR SEQ ID NO:22:

(i) SEQUENCE CHARACTERISTICS:
    (A) LENGTH: 22 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "primer"

(xi) SEQUENCE DESCRIPTION: SEQ ID NO:22:

CACTTGCAAC TCCAGGAAGA CT                                        22

(2) INFORMATION FOR SEQ ID NO:23:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:23:

AGACAAGTGA TTTTTGAGGA GTC                                       23

(2) INFORMATION FOR SEQ ID NO:24:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:24:

AACAACAAAG AGCAGGAAGA GATGG                                     25

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:25:

CTTCTGCCTC ATATCCAGGC                                           20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:26:

ACCTTGGTGA GAGTCGCCAG                                           20

(2) INFORMATION FOR SEQ ID NO:27:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:27:

ATCACCACTC CCAACCTGCC                                                    20

(2) INFORMATION FOR SEQ ID NO:28:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:28:

ATGCCTTCAG GATGCAGGCA                                                    20

(2) INFORMATION FOR SEQ ID NO:29:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:29:

ACATTTGCAA TTTGTACAGC                                                    20

(2) INFORMATION FOR SEQ ID NO:30:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:30:

GCCCGCTCAT GGGATGTG                                                      18

(2) INFORMATION FOR SEQ ID NO:31:

(i) SEQUENCE CHARACTERISTICS:
           (A) LENGTH: 21 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "primer"

(xi) SEQUENCE DESCRIPTION: SEQ ID NO:31:

AAGACTCTCT CCCCTGCCCT C                                                  21

(2) INFORMATION FOR SEQ ID NO:32:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:32:

GAAGTCTTAG TGATCGATGC AG                        22

(2) INFORMATION FOR SEQ ID NO:33:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:33:

AGAGGTCCCA GCGTGAGTGT                          20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:34:

AGACCAGAAG GAGCTGAGGG                          20

(2) INFORMATION FOR SEQ ID NO:35:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:35:

ACAGATGTAT ACAATTCAGC AG                        22

(2) INFORMATION FOR SEQ ID NO:36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:36:

CACCTAAAAC TTCAAAGGAC TG                        22

(2) INFORMATION FOR SEQ ID NO:37:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:37:

ATAGGGCATC GTGAC    15

(2) INFORMATION FOR SEQ ID NO:38:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:38:

ATAGGGCCTC GTGAC    15

(2) INFORMATION FOR SEQ ID NO:39:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:39:

GTGTGTTTTC CCCAGT    16

(2) INFORMATION FOR SEQ ID NO:40:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:40:

TGTGTGTTTT TCCCAGT    17

(2) INFORMATION FOR SEQ ID NO:41:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:41:

TGTTATAACG ACTACAA    17

(2) INFORMATION FOR SEQ ID NO:42:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:42:

TGTAGTCATT ATAACAG                                                17

(2) INFORMATION FOR SEQ ID NO:43:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:43:

AGGGCATGAC AGAGAC                                                 16

(2) INFORMATION FOR SEQ ID NO:44:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:44:

GTCTCTATCA TGCCCT                                                 16

(2) INFORMATION FOR SEQ ID NO:45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:45:

GTCACTTGTG ATCACTG                                              17

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:46:

GTCACTTGAG ATCACTG 17

(2) INFORMATION FOR SEQ ID NO:47:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:47:

TGTTTGTTGA TTGTTCA 17

(2) INFORMATION FOR SEQ ID NO:48:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:48:

TGAACAATAA ACAAACA 17

(2) INFORMATION FOR SEQ ID NO:49:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:49:

ATCTCCCCAG GACCATC 17

(2) INFORMATION FOR SEQ ID NO:50:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:50:

GATGGTCCTT GGGAGAT 17

(2) INFORMATION FOR SEQ ID NO:51:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:51:

```
GTGTCGCTTC TGGCATCTGT CCTTCTGG                                                    28

(2) INFORMATION FOR SEQ ID NO:52:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:52:

TACCCAGAAC AACGGCAGCT TCTTCCACT                                                   29

(2) INFORMATION FOR SEQ ID NO:53:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:53:

CCGGTTACCT TCTGCTGTAC AGCCCAGAAC AACGGCAGCT TCTTCCATC                             49

(2) INFORMATION FOR SEQ ID NO:54:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:54:

Ile Glu Ile Phe Thr Asp Leu Ser Ser Arg Phe
1               5                   10

(2) INFORMATION FOR SEQ ID NO:55:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:55:

Lys Thr Asp Thr Leu Glu Asp Leu Phe Pro
1               5                   10

(2) INFORMATION FOR SEQ ID NO:56:

(i) SEQUENCE CHARACTERISTICS:
        (A) LENGTH: 10 amino acids
        (B) TYPE: amino acid
        (C) STRANDEDNESS:
        (D) TOPOLOGY: linear
```

```
        (ii) MOLECULE TYPE: peptide (v) FRAGMENT TYPE: internal (xi) SEQUENCE DESCRIPTION: SEQ ID NO:56:

Leu Tyr Arg Glu Thr Asn Glu Pro Val Lys
1               5                   10

(2) INFORMATION FOR SEQ ID NO:57:

(i) SEQUENCE CHARACTERISTICS:
             (A) LENGTH: 6 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:57:

Thr Arg Thr Phe Asn Thr
1               5

(2) INFORMATION FOR SEQ ID NO:58:

(i) SEQUENCE CHARACTERISTICS:
             (A) LENGTH: 10 amino acids
             (B) TYPE: amino acid
             (C) STRANDEDNESS:
             (D) TOPOLOGY: linear (ii) MOLECULE TYPE: peptide (v) FRAGMENT TYPE: internal (xi) SEQUENCE DESCRIPTION: SEQ ID NO:58:

Ile Met Ala Thr Pro Glu Gln Val Gly Lys
1               5                   10
```

METHOD TO DETERMINE PREDISPOSITION TO HYPERTENSION

CROSS-REFERENCE TO RELATED APPLICATION

The present application is a continuation-in-part of application Ser. No. 09/092,988, filed Jun. 8, 1998, which is a continuation of application Ser. No. 08/319,545, filed Oct. 7, 1994, now U.S. Pat. No. 5,763,168, which is a continuation-in-part of application Ser. No. 07/952,442, filed Sep. 30, 1992, now U.S. Pat. No. 5,374,525.

This invention was made with Government support under Grant Nos. HL24855 and HM45325, awarded by the National Institutes of Health, Bethesda, Md. The United States Government has certain rights in the invention.

BACKGROUND OF THE INVENTION

The present invention relates to molecular variants of the angiotensinogen gene. The present invention further relates to the diagnosis of these variants for the determination of a predisposition to hypertension, the determination of the prognosis of the predisposition to hypertension, and the management of hypertension.

The publications and other materials used herein to illuminate the background of the invention, or provide additional details respecting the practice, are incorporated by reference herein, and for convenience are respectively grouped in the appended List of References.

Hypertension is a leading cause of human cardiovascular morbidity and mortality, with a prevalence rate of 25–30% of the adult Caucasian population of the United States (JNC Report, (1985). The primary determinants of essential hypertension, which represents 95% of the hypertensive population, have not been elucidated in spite of numerous investigations undertaken to clarify the various mechanisms involved in the regulation of blood pressure. Studies of large populations of both twins and adoptive siblings, in providing concordant evidence for strong genetic components in the regulation of blood pressure (Ward, 1990), have suggested that molecular determinants contribute to the pathogenesis of hypertension. However, there is no information about the genes actually involved, about the importance of their respective effects on blood pressure, or about their interactions with each other and the environment.

Among a number of factors for regulating blood pressure, the renin-angiotensin system plays an important role in salt-water homeostasis and the maintenance of vascular tone; stimulation or inhibition of this system respectively raises or lowers blood pressure (Hall et al., 1990), and may be involved in the etiology of hypertension. The renin-angiotensin system includes the enzymes renin and angiotensin-converting enzyme and the protein angiotensinogen (AGT). Angiotensinogen is the specific substrate of renin, an aspartyl protease. The structure of the AGT gene has been characterized (Gaillard et al., 1989; Fukamizu et al., 1990).

The human AGT gene contains five exons and four introns which span 13 Kb. The first exon (37 bp) codes for the 5' untranslated region of the mRNA. The second exon codes for the signal peptide and the first 252 amino acids of the mature protein. Exons 3 and 4 are shorter and code for 90 and 48 amino acids, respectively. Exon 5 contains a short coding sequence (62 amino acids) and the 3'-untranslated region.

Plasma angiotensinogen is primarily synthesized in the liver under the positive control of estrogens, glucocorticoids, thyroid hormones, and angiotensin II (Clauser et al., 1989) and secreted through the constitutive pathway. Cleavage of the amino-terminal segment of angiotensinogen by resin releases a decapeptide prohormone, angiotensin-I, which is further processed to the active octapeptide angiotensin II by the dipeptidyl carboxypeptidase angiotensin-converting enzyme (ACE). Cleavage of angiotensinogen by renin is the rate-limiting step in the activation of the renin angiotensin system (Sealey et al., 1990). Several observations point to a direct relationship between plasma angiotensinogen concentration and blood pressure; (1) a direct positive correlation (Walker et al., 1979); (2) high concentrations of plasma angiotensinogen in hypertensive subjects and in the offspring of hypertensive parents compared to normotensives (Fasola et al., 1968); (3) association of increased plasma angiotensinogen with higher blood pressure in offspring with contrasted parental predisposition to hypertension (Watt et al., 1992); (4) decreased or increased blood pressure following administration of angiotensinogen antibodies (Gardes et al., 1982) or injection of angiotensinogen (Menard et al., 1991); (5) expression of the angiotensinogen gene in tissues directly involved in blood pressure regulation (Campbell and Habener, 1986); and (6) elevation of blood pressure in transgenic animals overexpressing angiotensinogen (Ohkubo et al., 1990; Kimura et al., 1992).

Recent studies have indicated that renin and ACE are excellent candidates for association with hypertension. The human renin gene is an attractive candidate in the etiology of essential hypertension: (1) renin is the limiting enzyme in the biosynthetic cascade leading to the potent vasoactive hormone, angiotensin II; (2) an increase in renin production can generate a major increase in blood pressure, as illustrated by renin-secreting tumors and renal artery stenosis; (3) blockade of the renin-angiotensin system is highly effective in the treatment of essential hypertension as illustrated by angiotensin I-converting enzyme inhibitors; (4) genetic studies have shown that renin is associated with the development of hypertension in some rat strains (Rapp et al. 1989; Kurtz et al. 1990); (5) transgenic animals bearing either a foreign renin gene alone (Mullins et al. 1990) or in combination with the angiotensinogen gene (Ohkubo et al. 1990) develop precocious and severe hypertension.

The human ACE gene is also an attractive candidate in the etiology of essential hypertension. ACE inhibitors constitute an important and effective therapeutic approach in the control of human hypertension (Sassaho et al. 1987) and can prevent the appearance of hypertension in the spontaneously hypertensive rat (SHR) (Harrop et al., 1990). Recently, interest in ACE has been heightened by the demonstration of linkage between hypertension and a chromosomal region including the ACE locus found in the stroke-prone SHR (Hilbert et al., 1991; Jacob et al., 1991).

The etiological heterogeneity and multifactorial determination which characterize diseases as common as hypertension expose the limitations of the classical genetic arsenal. Definition of phenotype, model of inheritance, optimal familial structures, and candidate-gene vs. general-linkage approaches impose critical strategic choices (Lander et al., 1986; White et al., 1987; Lander et al., 1989; Lalouel, 1990; Lathrop et al., 1991). Analysis by classical likelihood ratio methods in pedigrees is problematic due to the likely heterogeneity and the unknown mode of inheritance of hypertension. While such approaches have some power to detect linkage, their power to exclude linkage appears limited. Alternatively, linkage analysis in affected sib pairs is a robust method which can accommodate heterogeneity and incomplete penetrance, does not require any a priori formulation of the mode of inheritance of the trait and can be used to place upper limits on the potential magnitude of effects exerted on a trait by inheritance at a single locus. (Blackwelder et al., 1985; Suarez et al., 1984).

It was an object of the present invention to determine a genetic association with essential hypertension. It was a further object to utilize such an association to identify persons who may be predisposed to hypertension leading to better management of the disease.

SUMMARY OF THE INVENTION

The present invention relates to identification of a molecular basis of human hypertension. More specifically, the present invention has identified that angiotensinogen (AGT) is involved in the pathogenesis of hypertension. Molecular variants of the AGT gene contribute to an individual's susceptibility to the development of hypertension. The analysis of the AGT gene will identify subjects with a genetic predisposition to develop essential hypertension or pregnancy-induced hypertension. The management of hypertension in these subjects could then be more specifically managed, e.g., by dietary sodium restriction, by carefully monitoring blood pressure and treating with conventional drugs, by the administration of renin inhibitors or by the administration of drugs to inhibit the synthesis of AGT. The analysis of the AGT gene is performed by comparing the DNA sequence of an individual's AGT gene with the DNA sequence of the native, non-variant AGT gene. It has been found that an analysis of the AGT gene at the −20 nucleotide position can be used to determine the prognosis of the predisposition to hypertension, as determined by analyzing the gene at the −6 nucleotide position. Since the M235T molecular variant occurs in linkage disequilibrium with the G-6A molecular variant, analysis of the M235T molecular variant could be used in place of the G-6A molecular variant.

DETAILED DESCRIPTION OF THE INVENTION

The present invention is directed to the determination that molecular variants of the angiotensinogen (AGT) gene are involved in the pathogenesis of hypertension. The present invention surprisingly has found that molecular variants of the AGT gene contribute to development of hypertension in humans. The present invention is further directed to methods of screening humans for the presence of AGT gene variants which are associated with the predisposition of humans to develop essential hypertension or pregnancy-induced hypertension. Since a predisposition to hypertension can now be established by screening for molecular variants of the AGT gene, individuals at risk can be more closely monitored and treated before the disease becomes serious. It has been found that an analysis of the AGT gene at the −20 nucleotide position can be used to determine the prognosis of the predisposition to hypertension, as determined by analyzing the gene at the −6 nucleotide position. Since the M235T molecular variant occurs in linkage disequilibrium with the G-6A molecular variant, analysis of the M235T molecular variant could be used in place of the G-6A molecular variant.

Essential hypertension is one of the leading causes of human cardiovascular morbidity and mortality. Epidemiological studies of blood pressure in related individuals suggest a genetic heritability around 30% (Ward, 1990). The continuous, unimodal distribution of blood pressure in the general population as well as in the offspring of hypertensive parents (Hamilton et al., 1954) supports the hypothesis that several genes are involved in this genetic predisposition. However, there is no information about the genes actually involved, the importance of their respective effects on blood pressure, or their interactions with each other and the environment.

Genetic studies in animal models of hypertension have suggested an involvement of the two key enzymes of this system in the genesis of high blood pressure, renin (Rapp et al., 1989; Mullins et al., 1990; Kurtz et al., 1990), and angiotensin converting enzyme through linkage to a nearby marker (Hilbert et al., 1991; Jacob et al., 1991; Deng et al., 1992). The purpose of the present invention was to identify an association with hypertension. It was unexpectedly found that neither renin nor angiotensin-converting enzyme is associated with human hypertension. Instead, it was found that the angiotensinogen gene is involved in the pathogenesis of essential hypertension. The following were found: (1) genetic linkage between essential hypertension and AGT in affected siblings; (2) association between hypertension and certain molecular variants of AGT as revealed by comparison between cases and controls; (3) increased concentrations of plasma angiotensinogen in hypertensive subjects who carry a common variant of AGT strongly associated with hypertension; (4) persons with the most common AGT gene variant exhibited not only raised levels of plasma angiotensinogen but also higher blood pressure; and (5) the most common AGT gene variant was found to be statistically increased in women presenting preeclampsia during pregnancy, a condition occurring in 5–10% of all pregnancies. The association between renin, ACE or AGT and essential hypertension was studied using the affected sib pair method (Bishop et al., 1990) on populations from Salt Lake City, Utah and Paris, France, as described in further detail in the Examples. Only an association between the AGT gene and hypertension was found. The AGT gene was examined in persons with hypertension, and at least 15 variants have been identified. None of these variants occur in the region of the AGT protein cleaved by either renin or ACE. Identification of the AGT gene as being associated with essential hypertension was confirmed in a population study of healthy subjects and in women presenting preeclampsia during pregnancy.

Although molecular variants of the AGT gene have been established as predisposing a person to hypertension, it is not possible to determine at this time whether the observed molecular variants of AGT directly affect function or whether they serve as markers for functional variants that have escaped identification by the molecular screening method used. When the sequence of human angiotensinogen is compared to that of rat angiotensinogen, and to other serine protease inhibitors (serpins) such as antithrombin-III and alpha-1-antitrypsin, the AGT gene variants M235T and T174M appear to occur in regions with little conservation (Carrell et al., 1986). By contrast, the variant Y248C, which was observed in the heterozygote state in only one pair of hypertensive siblings, constitutes a non-conservative substitution in a region well conserved among serpins. In addition to this predisposition encoded by common variants, rare variants such as Y248C and V388M have the potential to impart predispositions with unique clinical courses and severities.

As used herein, AGT gene variants are expressed either at the amino acid level, e.g., M235T in which the variant protein contains threonine at amino acid residue 235 instead of methionine, or at the nucleotide level, e.g., C-532T in which the variant gene contains thymidine at nucleotide −532 of the 5' sequence instead of cytosine of the native gene. Several mutations are set forth in Table 2.

When hypertensive siblings were stratified according to genotypes at residue 235, higher plasma concentrations of angiotensinogen were observed among carriers of M235T (F23,3=14.9, p<0.0001). Again, this result was observed independently in each sample. A correlation between plasma angiotensinogen concentration and blood pressure has already been observed (Walker et al., 1979). Taken together, these observations suggest a direct involvement of plasma angiotensinogen in the pathogenesis of essential hypertension. This conclusion is further strengthened by finding that the M235T variant was significantly associated not only with raised plasma angiotensinogen concentrations but also with increased blood pressure. See Example 8, below.

The present invention is corroborated by two additional findings: (1) plasma angiotensinogen was higher in hypertensive subjects and in offspring of hypertensive parents than in normotensives (Fasola et al., 1968); and (2) in the Four-Corners study, angiotensinogen concentrations were significantly associated with increased blood pressure in the subset most likely to entail a genetic predisposition, namely the high blood pressure offspring of high-blood pressure parents (Watt et al., 1992). Because the plasma concentration of angiotensinogen is close to the $K_m$ of the enzymatic reaction between renin and angiotensinogen (Gould et al., 1971), a rise or fall in renin substrate can lead to a parallel change in the formation of angiotensin II (Cain et al., 1971; Menard et al., 1973; Arnal et al., 1991). Thus, it is conceivable that raised baseline levels could lead to mild overactivity of the renin-angiotensin system, and represent an altered homeostatic setpoint in predisposed individuals. Indeed, long-term administration of angiotensin II at suppressor doses has been shown to elevate blood pressure (Brown et al., 1981).

Recent studies suggest that not only plasma angiotensinogen, but also local expression in specific tissues, could contribute to blood pressure regulation. Yongue et al. (1991) observed increased expression of angiotensinogen in the anterioventral hypothalamus and in contiguous areas of the brain in SHR rats in comparison to normotensive control WKY rats, but they found no difference in liver expression. A possible role of angiotensinogen in the central nervous system is further supported by experimental overexpression of the AGT gene in transgenic rats: plasma concentrations were raised, but high blood pressure was observed only in a transgenic line displaying proper tissue-specific expression of the transgene in the brain (Kimura et al., 1992). Furthermore, evidence for local synthesis of the different components of the renin angiotensin system in the kidney has accumulated and an alteration of the regulation of angiotensinogen expression by sodium has been observed in SHR rats (Pratt et al., 1989).

Without being bound by any theory of action, it is possible that some molecular variants of angiotensinogen, such as those identified or tagged by the variant at residue 235 or the variant at the −6 nucleotide, lead to increased plasma or tissue angiotensinogen as a result of either increased synthetic rate, altered reaction constants with renin, or increased residence time through complex formation with self or with other extracellular proteins. This could lead to a small increase in baseline or in reactive production of angiotensin II, accounting for a slight overreactivity of the renin angiotensin system in response to sodium and environmental stressors. Over decades, this in turn could promote sodium retention as a result of chronic stimulation of aldosterone secretion, vascular is hypertrophy and increased peripheral vascular resistance as a result of chronic elevation of angiotensin II formation, or abnormal stimulation of the sympathetic nervous system mediated by enhanced production of angiotensin II in relevant areas of the brain.

In addition to establishing the analysis for the G-6A and/or M235T molecular variants (see U.S. Pat. Nos. 5,374, 525 and 5,763,168), it has now been established that analysis of the −20 position of the ACT gene is important for determining the prognosis of hypertension. Specifically, it has been discovered that the native A-20 modulates the effect of the A-6 variant That is, the level of the transcriptional activity of the A-20/A-6 gene is lower than the C-20/A-6 gene. However, the level of transcriptional activity is still higher than that for the native A-20G-6 gene. Consequently, the analysis of the −20 position of the AGT gene is useful for determining the severity of the hypertension which could result from the 6–6A variant and/or for determining the severity of the risk for the predisposition to hypertension. The −20 position thus provides a prognostication for hypertension.

The identification of the association between the AGT gene and hypertension permits the screening of individuals to determine a predisposition to hypertension. Those individuals who are identified at risk for the development of the disease may benefit from dietary sodium restriction, can have their blood pressure more closely monitored and be treated at an earlier time in the course of the disease. Such blood pressure monitoring and treatment may be performed using conventional techniques well known in the art.

To identify persons having a predisposition to hypertension, the AGT alleles are screened for mutations. Plasma angiotensinogen levels of persons carrying variants of the AGT gene are then examined to identify those at risk. Any human tissue can be used for testing the DNA. Most simply, blood can be drawn and DNA extracted from the cells of the blood. The AGT alleles are screened for mutations either directly or after cloning the alleles.

The alleles of the AGT gene in an individual to be tested are cloned using conventional techniques. For example, a blood sample is obtained from the individual. The genomic DNA isolated from cells in this sample is partially digested to an average fragment size of approximately 20 kb. Fragments in the range from 18–21 kb are isolated. The resulting fragments are ligated into an appropriate vector. The sequences are then analyzed as described herein.

Alternatively, polymerase chain reactions (PCRs) are performed with primer pairs for the 5' region or the exons of the AGT gene. Examples of such primer pairs are set forth in Table 1. PCRs can also be performed with primer pairs based on any sequence of the normal AGT gene. For example, primer pairs for the large intron can be prepared and utilized. Finally, PCR can also be performed on the mRNA. The amplified products are then analyzed as described herein.

TABLE 1

Primers Used for the Detction of Molecular Variants of AGT

| Location | Primer 1 (SEQ ID NO:) | Primer 2 (SEQ ID NO:) |
|---|---|---|
| 5' | ACCATTTGCAATTTGTACAGC (1) | GCCCGCTCATGGGATGTG (2) |
| 5' | AAGACTCTCCCCTGCCCCTCT (3) | GAAGTCTTAGTGATCGATGCAG (4) |

TABLE 1-continued

Primers Used for the Detction of Molecular Variants of AGT

| Location | Primer 1 (SEQ ID NO:) | Primer 2 (SEQ ID NO:) |
|---|---|---|
| 5'Ex1 | AGAGGTCCCAGCGTGAGTGT (5) | AGACCAGAAGGAGCTGAGGG (6) |
| Ex2 | GTTAATAACCACCTTTCACCCTT (7) | GCAGGTATGAAGGTGGGGTC (8) |
| Ex2 | AGGCCAATGCCGGGAAGCCC (9) | ATCAGCCCTGCCCTGGGCCA (10) |
| Ex2 | GATGCGCACAAGGTCCTGTC (11) | GCCAGCAGAGAGGTTTGCCT (12) |
| Ex3 | TCCCTCCCTGTCTCCTGTCT (13) | TCAGGAGAGTGTGGCTCCCA (14) |
| Ex4 | TGGAGCCTTCCTAACTGTGC (15) | AGACACAGGCTCACACATAC (16) |
| Ex5 | GTCACCCATGCGCCCTCAGA (17) | GTGTTCTGGGGCCCTGGCCT (18) |

The alleles are tested for the presence of nucleic acid sequence differences from the normal allele by determining the nucleotide sequence of the cloned allele or amplified fragment and comparing it to the nucleotide sequence of the normal allele. Alternatively, there are six well known methods for a more complete, yet still indirect, test for confirming the presence of a predisposing allele:(1) single stranded conformation analysis (SSCA) (Orita et al., 1989); (2) denaturing gradient gel electrophoresis (DGGE) (Wartell et al., 1990; Sheffield et al., 1989); (3) RNase protection assays (Finkelstein et al., 1990; Kinszler et al., 1991); (4) allele-specific oligonucleotides (ASOs) (Conner et al., 1983); (5) the use of proteins which recognize nucleotide mismatches, such as the E. coli mutS protein (Modrich, 1991); and, (6) allele-specific PCR (Ruano et al., 1989). For allele-specific PCR, primers are used which hybridize at their 3' ends to a particular AGT mutation. If the particular AGT mutation is not present, an amplification product is not observed. Amplification Refractory Mutation System (ARMS) can also be used, as disclosed in Published European Patent Application No. 0332435 and in Newton et al. (1989).

In the first three methods (SSCA, DGGE and RNase protection assay), a new electrophoretic band appears. SSCA detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type AGT gene coding sequence.

The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site −1 1 of the mismatch. Thus, when the annealed RNA preparation is separated on an electrophoretic gel matrix, if a mismatch has been detected and cleaved by BNase A, an RNA product will be seen which is smaller than the full length duplex RNA for the riboprobe and the mRNA or DNA. The riboprobe need not be the full length of the AGT mRNA or gene but can be a segment of either. If the riboprobe comprises only a segment of the AGT mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR before hybridization. Changes in DNA of the AGT gene can also be detected using Southern hybridization, especially if the changes are gross rearrangements, such as deletions and insertions.

DNA sequences of the AGT gene which have been amplified by use of PCR may also be screened using allele-specific probes. These probes are nucleic acid oligomers, each of which contains a region of the AGT gene sequence harboring a known mutation. For example, one oligomer may be about 30 nucleotides in length, corresponding to a portion of the AGT gene sequence. By use of a battery of such allele-specific probes, PCR amplification products can be screened to identify the presence of a previously identified mutation in the AGT gene. Hybridization of allele-specific probes with amplified AGT sequences can be performed, for example, on a nylon filter. Hybridization to a particular probe under stringent hybridization conditions indicates the presence of the same mutation in the DNA sample as in the allele-specific probe.

Mutations falling outside the coding region of AGT can be detected by examining the noncoding regions, such as introns and regulatory sequences near or within the AGT gene. An early indication that mutations in noncoding regions are important may come from Northern blot experiments that reveal messenger RNA molecules of abnormal size or abundance in hypertensive patients as compared to control individuals.

Alteration of AGT mRNA expression can be detected by any techniques known in the art. These include Northern blot analysis, PCR amplification and RNase protection. Diminished mRNA expression indicates an alteration of the wild-type ATG gene. Alteration of wild-type AGT genes can also be detected by screening for alteration of wild-type angiotensinogen. For example, monoclonal antibodies immunoreactive with angiotensinogen can be used to screen a tissue. Lack of cognate antigen would indicate a AGT gene mutation. Antibodies specific for products of mutant alleles could also be used to detect mutant AGT gene product. Such immunological assays can be done in any convenient formats known in the art. These include Western blots, immunohistochermical assays and ELISA assays. Any means for detecting an altered angiotensinogen can be used to detect alteration of wild-type AGT genes. Finding a mutant AGT gene product indicates alteration of a wild-type AGT gene.

Further details of a suitable PCR method are set forth in the Examples. The AGT alleles can be screened for the variants set forth in Table 2, as well as other variants using these techniques or those techniques known in the art.

purposes of the present study, affection status was defined as a diagnosis of hypertension requiring treatment with antihypertensive medication prior to age 60, and the absence of diabetes mellitus or renal insufficiency; the study sample comprises 309 siblings (165 women, 144 men). All but three sibling pairs were Caucasians (one was Asian, two Hispanic) and their relevant clinical characteristics are indicated in Table 3. The 132 affected sibships are composed of 102 duos, 20 trios, seven quartets, one quintet, and two sextets of hypertensive siblings.

B. Paris. Selection of hypertensive families with a high prevalence of essential hypertension was conducted through ascertainment of hypertensive probands referred to the Hypertension Clinic of the Broussais Hospital in Paris, as previously described (Corvol et al., 1989). The 83 French sibships were collected through index patients who satisfied the following criteria: (1) onset of hypertension before age 60; (2) established hypertension defined either by chronically treated hypertension (n=156) or by a diastolic blood

TABLE 2

Molecular Variants in the Angiotensinogen Gene

| | | | Substitution | | Allele Frequency | |
| | | | | | Salt Lake City[1] | Paris[2] |
| Variant | Location | Position[3] | Nucleotide | Amino Acid | H/C | H/C |
|---|---|---|---|---|---|---|
| 1 | 5' | −532 | C→T | | .13/.12 | .11/n.d. |
| 2 | 5' | −386 | G→A | | .04/.04 | .02/n.d. |
| 3 | 5' | −218 | G→A | | .11/.10 | .08/n.d. |
| 4 | 5' | −18 | C→T | | .13/.13 | .19/n.d. |
| 5 | 5' | −6 and −20 | G→A and A→C | | .19/.14 | .18/n.d. |
| 6 | Ex1 | +10 | C→T | untranslated | 1 ind/0 | 0/n.d. |
| 7 | Ex2 | +521 | C→T | T→M (174) | .18/.08[4] | .17/.08[4] |
| 8 | Ex2 | +597 | T→C | P→P (199) | 1 ind/0 | 0/n.d. |
| 9 | Ex2 | +704 | T→C | M→T (235) | .49/.36[5] | .52/.38[4] |
| 10 | Ex2 | +743 | A→G | Y→C (248) | 1 ind/0 | 0/n.d. |
| 11 | Ex3 | +813 | C→T | N→N (271) | 1 ind/0 | 0/0 |
| 12 | Ex3 | +1017 | G→A | L→L (339) | .05/.08 | .06/n.d. |
| 13 | Int3 | −13[6] | A→G | | .07/.11 | .08/n.d. |
| 14[7] | Ex4 | +1075 | C→A | L→M (359) | .005/.01 | n.d./n.d. |
| 15 | Ex4 | +1162 | G→A | V→M (388) | 0/0 | 0/1 ind |

[1]Salt Lake City; 90 controls, 36 index patients from most severely affected pairs.
[2]Paris: 98 controls, 43 index patients from most severely affected pairs.
[3]Position is with reference to transcription start site.
[4]$p < 0.01$
[5]$p < 0.05$
[6]Position relative to beginning of exon 4.
[7]Variant previously described supressing a PstI site (Kunapuli and Kumer, 1986).
H/C Hypertensive/Control
n.d. Not Done
1 ind 1 Individual detected with the corresponding molecular variant.

The present invention is further detailed in the following Examples, which are offered by way of illustration and are not intended to limit the invention in any manner. Standard techniques well known in the art or the techniques specifically described below are utilized.

EXAMPLE 1

Selection of Sibships with Multiple Hypertensive Subjects

A. Salt Lake City. Families with two or more hypertensive siblings were characterized and sampled from "Health Family Tree" questionnaires collected from the parents of 40,000 high school students in Utah. The characteristics of this population-based selection of hypertensive sibships have been described previously (Williams et al., 1988). For pressure greater than 95 mmHg at two consecutive visits for those without antihypertensive treatment (n=34, mean diastolic blood pressure=103.8+13.1 mmHg); (3) absence of secondary hypertension, established by extensive inpatient work-up when clinically indicated; and (4) familial history of early onset (before age 60) of hypertension in at least one parent and one sibling. Patients with exogenous factors that could influence blood pressure were eliminated, in particular those with alcohol intake of more than four drinks per day or women taking oral contraceptives. Other exclusion criteria were a body mass index (BMI=weight/height$^2$) greater than 30 kg/m$^2$, the presence of diabetes mellitus, or renal insufficiency; the total sample consisted of 83 hypertensive sibships with 62 duos, 19 trios, 1 quartet and 1 quintet. All subjects were Caucasians, and relevant clinical characteristics are summarized in Table 3, below.

C. Controls. In Salt Lake City, 140 controls were defined as the grandparents of the Utah families included in the CEPH data base (Centre d'Etude du Polymorphisme Humain), a random panel of healthy families with large sibship size that serves as reference for linkage studies (Dausset et al., 1990). The French controls were 98 healthy normotensive subjects who had been selected in the context of a previous case-control study (Soubrier et al., 1990). Both samples included only Cucasians.

TABLE 3

Clinical Characteristics of the Hypertensive Siblings

|  | Salt Lake City | Paris |
|---|---|---|
| Sibships (pairs) | 132 (244) | 83 (135) |
| Subjects (m/f) | 309 (144/165) | 190 (99/91) |
| Age (years) | 49.4 (±7.4) | 52.3 (±9.9) |
| Age dx (years) | 39.4 (±9.6) | 40.4 (±11.7) |
| SBP (mmHg) | 127.8 (±15.6) | 156.0 (±12.6) |
| DBP (mmHg) | 80.0 (±99) | 98.2 (±12.6) |
| Rx (%) | 309 (100%) | 158 (82%) |
| B.M.I. (kg/m$^2$) | 29.7 (±5.5) | 24.9 (±3.0) |

Age dx: Age of diagnosis
SBP and DBP: Systolic and Diastolic Blood Pressure
B.M.I.: Body Mass Index
Unless otherwise stated, values are indicated as mean ± 1 S.D.

EXAMPLE 2

General Methods for Analysis of Linkage With Renin

A. Experimental Protocols. The experimental protocols using the French populations were conducted as previously described (Soubrier et al., 1990). Briefly, two probes were used to detect the diallelic RFLPs of three restriction enzymes. A 1.1 kb human renin cDNA fragment (Soubrier et al., 1983) was used to detect the HindIII polymorphism and a 307 bp genomic DNA fragment located in the 5' region of the renin gene (Soubrier et al., 1986) was used to detect the TaqI and HinfI polymorphisms. These two probes were labeled at high specific activity ($4 \times 10^9$ to $8 \times 10^9$ cpm/mg) with the random primer labelling method (Feinberg et al., 1983). Human genomic DNA was digested by TaqI, HinfI, or HindIII (New England Biolabs, Beverly, Mass.) and subjected to electrophoresis through an agarose gel (0.7% or 1.2%). After alkaline transfer to a nylon membrane (Hybond-N+, Amersham), hybridization to the corresponding probe, washing under high stringency conditions, and autoradiography, each restriction endonuclease detected the following biallelic RFLPs: 11 kb and 9.8 kb alleles (TaqI), 1.4 kb and 1.3 kb alleles (HinfI), and 9.0 kb and 6.2 kb alleles HindIII). These polymorphisms and their frequencies were in accordance with those previously described (Frossard et al., 1986 a,b; Masharani, 1989; Noftilan et al., 1989).

B. Analysis of RFLP Frequencies. For each RFLP, allele frequencies were determined from the genotype frequencies that had been previously established in 120 normotensives and 102 hypertensives (Soubrier et al., 1990). These frequencies satisfied the Hardy-Weinberg equilibrium. The informativeness of each biallelic RFLP, estimated by polymorphism information content (PIC) was, respectively, 0.16 (TaqI), 0.33 (HindIII), and 0.27 (HinfI). In spite of linkage disequilibriums between the HinfI, HindIII and HinfI TaqI polymorphisms, the combination of the three RFLPs led to a marked improvement in the marker's informativeness (PIC=0.65), corresponding to 70% of heterozygosity.

C. Construction of Haplotypes. The haplotypes were deduced from the combination of the three diallelic RFLPs. By the presence or absence of each restriction enzyme site, it was possible to define 8 ($2^3$) different haplotypes and 27 ($3^3$) genotypes. The haplotype frequencies have been previously estimated on a hypertensive population (Soubrier et al., 1990), with a maximum likelihood technique according to Hill's method (Hill, 1975). These haplotypes were used as a new multiallelic system in which each allele corresponded to one haplotype, numbered by its order frequency. These frequencies enabled us to compute the expected values of the number of alleles shared by a sibship under the hypothesis of an independent segregation of the renin gene marker and hypertension.

D. Comparison of Sib Genotypes. In 12 sibships, it was not possible to determine with certainty each haplotype—the presence of double or triple heterozygosity in the restriction enzyme sites—in spite of the analysis of other members of the same family. In these cases, the relative different parental mating type probabilities were calculated according to the haplotype frequencies. Then, the probabilities of the genotypes of each sib pair were deduced conditional to each parental mating type. For each sibship, the concordance between sibs was calculated as the mean of all possible concordances according to their relative probabilities. Because of the absence of one or two parental genotypes in 40 of the 57 sibships, and of the absence of complete heterozygosity of the renin marker, the alleles shared in common by one sib pair were assumed to be identical by state (i.b.s.), rather than identical by descent (i.b.d.). The concordance between the sib genotypes could be total (i.b.s.=1), partial (i.b.s.=½), or absent (i.b.s.=0). Under the null hypothesis of no linkage, the mean number of identical market alleles shared by a set of sib pairs (and its variance) is not affected by whether or not some of the sib pairs belong to the same sibship (Suarez et al., 1983; Blackwelder et al., 1985). Thus, the renin genotypes were compared for each sib pair and all the information contained in each sibship was taken into account by adding the concordances between all different sib pairs.

E. Comparison of the Expected Concordance Values. The expected proportions of alleles shared by both sibs were computed according to Lange (1986). This statistical method first calculates the probabilities of the different possible parental mating types taking into account the allelic frequencies and then the expected probabilities of total, half, or null concordance between sibs. It is thus possible to calculate the mean and the variance of the expected concordance for different sibship sizes under the null hypothesis of no linkage. The final t statistic is a one-sided Student's test adding the contributions of the different sibships.

Taking into account the possible bias in ascertainment of the size of the sibships, several authors have proposed different weights (w) to maximize the power of this statistic. In addition to $w_1=1$, we tested $w_2=1/\text{Var}(Z)$ ½ (Suarez et al., 1983; Motro et al., 1985) and $W_3=(s-1)$ ½$\text{Var}(Z_s)$ ½ (Hodge, 1984), where s represents the size of the affected sibship and Z, the statistic reflecting the allelic concordance for each sibship size (Lange, 1986).

EXAMPLE 3

General Methods for Analysis with ACE

A. Genotypes.
(1) The hGH-A1819 primers were designed from the published sequence flanking the eighteenth and nineteenth Alu elements of the hGH gene (Chen et al., 1989):

5'-ACTGCACTCCAGCCTCGGAG-3' (SEQ ID NO:19),
5'-ACAAAAGTCCTTTCTCCAGAGCA-3' (SEQ ID NO:20). Polymerase chain reactions (PCR) were performed using 100 ng of genomic DNA in a total volume of 20 ml containing 1×PCR Buffer (Cetus), 125 mM dNTPs, 150 pmol primers, 2mCiα $^{32}$P-dCTP. After an initial denaturation step (4 min at 94° C.), each of the 30 cycles consisted of 1 min at 94° C., 45 s at 63° C. and 30 s at 720° C., followed by a final elongation step (7 min at 72° C.). PCR reactions were performed in 96-well microtitre plates, using a Techne 2 apparatus. After completion, 20 ml of formamide with 10 mM EDTA was added to each reaction and, after denaturation at 94° C. for 5 min, 1 ml of this mixture was loaded on a 6% acrylaride gel containing 30% formarmide, 7M Urea, 135 mM Tris HCl, 45 mM boric acid and 2.5 mM EDTA. Gels were run at 70 W for 4 hr and were exposed 6–12 hr for autoradiography.

(2) ACE diallelic polymorphism was genotyped by enzymatic amplification of a segment in intron 16, with the 190 and 490 bp alleles resolved by a 1.5% agarose gel (Riget et al., 1992).

B. Genetic Mapping.

The chromosome 17 markers used in the genetic map were developed in the Department of Human Genetics of the University of Utah (Nakamura et al., 1988). The pairwise lod scores and recombination estimates (r) were determined from the analysis of 35 and 11 CEPH reference families for the ACE and hGH markers, respectively, using LINKAGE (Lathrop et al., 1984). No. recombination between ACE and hGH was detected from this pairwise analysis. Map order and recombination estimates of the chromosome 17 markers have then been determined using the CILINK subroutine. The placement of ACE has been determined by linkage to this genetic map in which the order and recombination frequencies between all other markers, including hGH, have been fixed at their maximum likelihood values.

C. Sib Pair Analysis.

All sib pairs from multiplex sibships were considered as independent, and the statistic was based on the mean number of alleles shared (Blackwelder et al., 1985). In the absence of parental genotypes, the sharing of alleles was scored as i.b.s. For each sibship size, the expectation of the mean number of alleles shared i.b.s. and its variance were calculated as described previously (Lange, 1986). The results show a 0.08% excess of alleles shared (95% confidence interval ±6.9%). For all pairs given equal weight, the one-sided t value is 0.02 (p=0.45). Weighting the contributions of multiplex sibships according to Hodge (1984) gives a final t value of 0.01 (p=0.49).

EXAMPLE 4

General Methods of Analysis of Linkage With AGT

A. Genotyping GT Alleles at the AGT Locus.

AGT genotypes were established by means of a highly informative dinucleotide repeat in the 3' flanking region of the AGT gene (Kotelevtsev et al., 1991). The primers used for the Paris sample were as published (K-primers); for the genotypes characterized in Utah, primers more distant to the (GT) repeat were designed:

5'-GGTCAGGATAGATCTCAGCT-3' (SEQ ID NO:21),
5'-CACTTGCAACTCCAGGAAGACT-3' (SEQ ID NO:22)

(U-Primers), which amplify a 167 bp fragment. In both laboratories, the polymerase chain reactions (PCRs) were performed using 80 ng of genomic DNA in a total volume of 20 µl containing 50 mM KCl, 5mM Tris-HCl, 0.01% gelatin, 1.5 mmol MgCl$_2$, 125 µM dNTPs, 20 pmol of each unlabeled primer, 10 pmol of one $^{32}$P-end labeled primer and 0.5 U of Taq polymerase (Perkin-Elmer Cetus, Norwalk, Conn.). After an initial denaturation step (4 min at 94° C.), each of the 30 cycles consisted of 1 min at 94° C., 1 min at 55° C. and 1 min at 72° C. (K-primers) or 45 sec at 94° C., 45 sec at 62° C. and 30 sec at 72° C. (U-primers). After completion, 20 µl of formamide with 10 mM EDTA was added to each reaction and, after denaturation at 94° C. for 5 min, 1 µl of this mixture was loaded on a 6% acrylamide gel containing 30% formamide, 7M Urea, 135 mM Tris-HCl, 45 mM Boric Acid and 2.5 mM EDTA (pH 7.8). Gels were run at 70W for 4 hours and were exposed 6–12 hours for autoradiography.

Genotypes were characterized in each of the hypertensive subjects and in 117 of their first degree relatives. Allelic frequencies were evaluated in 98 Caucasian normotensive controls from Paris, 140 Caucasian grandparents of CEPH pedigrees from Salt Lake City, and both sets of hypertensive index cases. At least 10 alleles were observed in each of the four groups, confirming the high heterozygosity (80%) of the marker. No significant difference in allelic frequencies was observed between controls and hypertensives from Paris ($X_6^2$=7.7, p=0.26); frequencies in controls were used as reference for linkage analysis in this sample. By contrast, controls and hypertensives from Salt Lake City exhibited significant differences in allelic frequencies ($X_6^2$=17.1, p=<0.01), primarily because the frequency of the most common allele was lower in hypertensives (0.36) than in controls (0.40); to avoid spurious bias on linkage tests, the frequencies estimated in hypertensive index cases were used for the analysis of the Salt Lake City sample.

B. Analysis of Linkage in Pairs of Hypertensive Siblings.

Conditional independence of segregating events -within sibships (Suarez et al., 1984) led to the generation of a total of 379 pairs of hypertensive siblings. Parental genotypes were determined directly or inferred from genotypes of non-hypertensive siblings in ten of the French sibships. In these sibships, alleles shared by siblings were considered as identical by descent (i.b.d.) and the appropriate statistical comparison employed (mean of 1.0 alleles shared per pair under independence). In the absence of parental genotypes (all Utah sibships, 73 French sibships), alleles shared by siblings were scored as identical by state (i.b.s) (Suarez et al., 1978; Blackwelder et al., 1985; Lange, 1986). For each sibship size, the expectation of the mean number of alleles shared i.b.s., and its variance, were calculated according to Lange (1986). The comparison between the observed and expected mean numbers of alleles shared by the pairs of siblings of every sibship yielded a one-sided Student t-test. The contribution of sibships of each size was weighted according to Hodge (Hodge, 1984). Predefined partitions of the data were examined sequentially so as to provide a parsimonious management of the degrees of freedom associated with multiple comparisons.

C. Molecular Variants Enzymatic Amplification of Segments of Angiotensinogen Gene.

From the known genomic structure of the human angiotensinogen gene (Gaillard et al., 1989), 10 different sets of oligonucleotides (Table 1) were designed to cover the 5' region containing the main regulatory elements and the five exons of the gene. They were chosen so as to generate products 200–300 bp long that would include at least 15 bp of the intronic sequence on either side of splice junctions.

For the conformational analysis of single-stranded DNA, samples were enzymatically amplified using 80 ng of genomic DNA in a total volume of 20 µl containing 50 mM KCl, 5 mM Tris-HCl (pH 8.3), 0.01% gelatin, 1.5 mmol MgCl$_2$, 125 µM dNTPs, 20 pmol of each unlabeled primer, 0.5 U of Taq polymerase and 0.15 µl of [α-$^{32}$P] dCTP (3000 Ci/ml).

Electrophoresis of DNA fragments under nondenaturing conditions. PCR products were diluted five-fold in a solution containing 95% formamide, 20 mM EDTA, 0.05% bromophenol blue, and 0.05% xylene cyanol. After denaturation at 90° C. for 4 min the samples were placed on ice, and 1.5 µaliquots loaded onto 5% nondenaturing polyacrylamide gels (49: 1 polyacrylamide:methylene 15 bis acrylamide) containing 0.5×TBE (1×TBE=90 mM Tris-borate, pH 7.8, 2 mM EDTA) (Orita et al., 1989). Each set of samples was electrophoresed under at least three conditions: a 10% glycerol gel at room temperature and at 4° C., and a gel without glycerol at 4 C. For the first two conditions, electrophoresis was carried out at 500 Volts, constant voltage, for 14–20 hours; for the third, electrophoresis was performed at 15 W, constant power, for 4–5 hours. The gels were dried and autoradiographed with an intensifying screen for 6–12 hours.

Direct sequencing of electrophoretic variants. Individual bands that presented mobility shifts with respect to wild type were sequenced as described by Hata et al. (1990), with some modifications. Each band was excised from the dried gel, suspended in 100 µl H$_2$O, and incubated at 37° C. for 1 hr. A 2-µl aliquot was subjected to enzymatic amplification in a 100-µl reaction volume, with specific primers augmented at their 5' ends with motifs corresponding to universal and reverse M13 sequencing primers. The double-stranded product resulting from this amplification was isolated by electrophoresis on a low-melting agarose gel and purified using GeneClean™ (Bio 101, La Jolla, Calif.). A second round of enzymatic amplification was usually performed under similar conditions, using reduced amounts of primers (5 picomol) and of dNTPs (50 µM), and the amplified product was spin-dialyzed with a Centricon 100™ column (Amicon, Beverly, Mass.). Direct sequencing of double-stranded DNA was performed on an ABI 373A DNA sequencer, using fluorescent M13 primers, Taq polymerase and a thermocycling protocol supplied by the manufacturer (Applied Biosystems, Foster City, Calif.).

Allele-specific oligonucleotide hybridization. To verify the presence of molecular variants identified by direct sequencing and to determine genotypes, oligonucleotide-specific hybridization was performed. After enzymatic amplification of genomic DNA, each product was denatured with 0.4 N NaOH for 5 min, then spotted in duplicate on nylon membranes (Hybond+,Amersham, Arlington Heights, Ill.), neutralized with 3M Na acetate and cross-linked with UV light. Each membrane was thereafter hybridized with $^{32}$P-end labeled oligonucleotide probes corresponding to wild-type and mutant sequences. After hybridization in 7% polyethylene glycol, 10% SDS, 50 mM sodium phosphate, pH 7.0, for 6 hours, the membranes were washed in 6×SSC, 0.1% SDS with a stringency corresponding to the calculated melting temperature of the probe. Six molecular variants were subjected to such a procedure (variants 3, 5, 7, 9, 10, 15 in Table 2). Variant 14 (L359M) was analyzed by the presence or absence of a PstI site (Kunapuli et al., 1986) in 140 Utah controls and in the 36 more severely hypertensive index cases from Utah.

D. Linkage Disequilibrium Between Marker and Variants of AGT.

Haplotype distribution of GT alleles and of variants observed at residues 174 and 235 were evaluated by maximum likelihood. The M235 allele was in strong linkage disequilibrium with the most common GT allele (16 repeats; GT16) while the M235T variant was found in combination with a wide range of GT alleles. The association between M235 and GT16 was consistent with the greater frequency of GT16 in controls than in hypertensives noted earlier. Because the M235T variant occurred in association with a variety of GT alleles, a greater frequency of M235T in cases would not induce spurious genetic linkage between hypertension and the GT marker.

E. Assay of Angiotensinogen.

Plasma angiotensinogen was measured as the generation of angiotensin I after addition of semi-purified human renin to obtain complete cleavage to angiotensin I; the amount of angiotensin I released was measured by radioimmunoassay and angiotensinogen was expressed in ng A-I/ml (Plouin et al., 1989).

EXAMPLE 5

Linkage Analysis Between Renin and Hypertension

The analysis of linkage between renin, the primary candidate, and hypertension was carried out using the methods described above in Example 2.

A. RFLP Alleles and Haplotype Frequencies.

Similar RFLP frequencies were observed in the 57 hypertensive sib pair probands and the hypertensive reference group was first verified. All RFLPs were in Hardy-Weinberg equilibrium and similar proportions were found in the two groups. Thus, the same haplotype frequencies were deduced from these three RFLPs with eight possible haplotypes and 70% heterozygosity. The six more frequent haplotypes were observed in the 133 hypertensive siblings.

B. Observed and Expected Concordances According to Each Sibship Size.

The 98 hypertensive sib pairs shared 141 i.b.s. alleles (mean ±1 standard deviation=1.44±0.60), while 133.4 (1.36±0.60) were expected under the hypothesis of no lnkage, corresponding to a mean excess of 0.08 allele with a 95% confidence interval of −0.04 to +0.20.

According to each sibship size, 63, 49, and 26 alleles were shared by the 41 pairs, 13 trios (39 pairs), and 3 quartets (18 pairs), respectively. The corresponding mean observed Z concordances were 0.77, 1.89, and 4.33. The comparison of the observed and expected concordances, computed in a unilateral statistic, was not significant (t=0.51, P=0.30).

C. Weights According to the Sibship Sizes.

There was a significant excess of i.b.s. allele sharing (13%) when only the 41 sib pairs were considered (63 observed vs. 55.8 expected alleles, t=1.93, P<0.03). However, this was negated bythe inclusion of the 13 trios with 4 alleles less than expected, and of the 3 quartets with an excess of only 1.5 alleles.

These variations are reflected by the different levels of the value according to the different weights that take into account the sibship size. While the t of 0.52 was computed with $w_1$=1, the use of $w_2$ and $w_3$, decreasing the weight given to the large sibships, increased the statistic although it remained nonsignificant: $t_2$=1.34, P=0.09 and $t_3$=1.16, P=0.12.

D. Discussion.

Ninety-eight hypertensive sib pairs from 57 independent sibships were analyzed The hypertensive sibs were selected if they had a strong predisposition to familial hypertension (at least one parent and one sibling), an early onset of the disease (40.7+12 years), and established essential hypertension. Three different RFLPs located throughout the renin gene (TaqI, HindIII, Hinfl) were used as genetic markers. The combination of these three RFLPs allowed the definition of eight haplotypes, of which six were observed. The allelic frequencies had been previously determined by the analysis of 102 hypertensive subjects (Soubrier et al., 1990) and were confirmed in the 57 hypertensive sib probands. Taking into account the incomplete heterozygosity of this renin marker (70%) and the absence of parental information in 40 of the 57 sibships, the alleles shared by the affected sibs were considered as identical by state and the appropriate statistical test was used (Lange 1986). No statistically significant difference was found between the observed frequencies of total, half, or null allelic concordances and those expected under the hypothesis of no linkage between the renin gene and hypertension. When the pairs were analyzed independently, these proportions were of 0.50 vs. 0.45, 0.43 vs. 0.48, and 0.07 vs. 0.07 for the observed vs. expected values, respectively, giving a chi-square (2 df)=1.21, which was not significant The most appropriate statistic, using the mean number of marker alleles shared by the sibs (Blackwelder et al., 1985) and adding the information obtained in each family according to the affected sibship size, did not demonstrate significance (t=0.51, P=0.30), with only a 5.7% excess of i.b.s. renin alleles shared by the 98 hypertensive sib pairs. When the reciprocal of the square root of the variance of the concordance index for each sibship size was used to maximize the power of the test (Motro et al., 1985), value increased (t=1.31) but remained nonsignificant (P=0.09). Thus, no association was found between renin and hypertension.

EXAMPLE 6

Linkage Analysis Between ACE and Hypertension

The analysis of linkage between ACE and hypertension was carried out using the methods described above in Example 3.

A. ACE Growth Hormone Linkage.

As sib pair linkage tests depend critically on high heterozygosity at the marker locus (Bishop et al., 1990), cosmids spanning the ACE locus were cloned but failed to identify an informative simple sequence repeat (data not shown). Since the ACE gene has been localized by inz situ hybridization to 17q23 (Mattei et al., 1989), a genetically well-characterized chromosomal region (Nakamura et al., 1988), the ACE locus was placed on the genetic map by linkage analysis in 35 CEPH pedigrees using a diallelic polymorphism (Riget et al., 1990, 1992). Analysis demonstrated strong linkage to markers fLB17.14, pCMM86 and PM8. Multilocus analysis localized the ACE locus between pCMM86 and PM8 (odds ratio favoring location in this interval=2000:1). The hGH gene, localized by in situ hybridization to the same region (Harper et al., 1982), has also shown strong linkage to these markers (Ptacek et al., 1991). Its sequence (Chen et al., 1989) enabled the development of a highly polymorphic marker based on AAAGT and AGT repeats lying between the eighteenth and nineteenth Alu repetitive sequences of this locus. The hGH-A2819 marker displayed 24 alleles and heterozygosity of 94.6% in 132 unrelated subjects. A similar hGH marker has been reported to show 82% heterozygosity in 22 unrelated subjects (Polymeropoulos et al., 1991). Pairwise linkage analysis using this marker in 11 CEPH pedigrees demonstrated complete linkage of the hGH and ACE loci in 109 meioses (log of the odds (lod) score=11.68). Multilocus analysis confirmed complete linkage between the ACE and hGH loci with a 95% confidence interval for recombination between these loci of ±0.02. This tight linkage permits use of the hGH marker as a surrogate for the ACE locus in linkage analysis with little or no loss of power.

B. Sib Pair Analysis.

The characteristics of hypertensive pedigrees ascertained in Utah have been previously described (see Example 1). All sibs analyzed were diagnosed by hypertensive before 60 years of age (mean 39.3±9.6 yr) and were on antihypertensive medication. Allele frequencies at ACE and hGH loci were compared between 132 controls (Utah grandparents belonging to the CEPH reference families) and 149 hypertensive pedigrees). The frequencies of the two ACE alleles were similar in the two groups (frequencies of the larger allele were 0.455 and 0.448, respectively), as were the frequencies of the 24 alleles at the hGH locus, indicating no linkage disequilibrium between the marker loci and hypertension. From the 149 hypertensive sibships, 237 sib pairs with the hGH marker were genotyped. In the absence of parental genotypes, allele sharing between sibs was scored as identical by state (i.b.s.) (Lange, 1986). The expected number of alleles shared in the total sample under the null hypothesis of no linkage of the marker locus and predisposition to hypertension as 254.8 (1.075 per sib pair); the observed number of alleles shared, 255, coincided with this expectation (t=0.01, ns). The high polymorphism of the hGH marker and the large number of sib pairs studied gives this analysis 80% power to detect a 10.36% excess in the number of alleles shared i.b.s., corresponding to a 12.02 or 13.06% excess of alleles identical by descent (i.b.d.) under a recessive or a dominant model, respectively.

C. Hypertensive Subgroups.

The power of such an analysis can be increased by stratifying an aetiologically heterogeneous population into more homogeneous subgroups. Six different subsets of hypertensive pairs were considered sequentially. As a possible enrichment of the genetic component determining high blood pressure, two subsets were selected: (1) 52 pairs in which both sibs had early onset of hypertension (prior to 40 years of age); (2) 31 sib pairs with more severe hypertension, in whom two or more medications were required for blood pressure control. No excess allele sharing was observed in either group. As a control for the potential influence of obesity, a significant confounding factor, we separately analyzed the 71 lean hypertensive pairs in which both sibs had a body mass index less than 20 kg m$^{-2}$ (mean 25.9±2.8 kg m$^{-2}$). Again, allele sharing did not depart from that expected under random segregation of the marker and hypertension.

It is of further interest to stratify for intermediate phenotypes which could be related to either the ACE or hGH loci. ACE plasma concentration shows evidence for a major gene effect but no relation to blood pressure in healthy subjects (Riget et al., 1990; Alhenc-Gelas et al., 1991). Chronic elevations of hGH can induce not only increased lean body mass and hypertension but also insulin resistance (Bratusch-Marrain et al., 1982), a common feature in both human hypertension (Ferrannini et al., 1987; Pollare et al., 1990) and SHR (Reaven et al., 1991). Sib pairs with (a) high lean body mass, (b) high fasting insulin levels and (c) high fasting insulin levels after adjustment for 25% body mass, since body mass is strongly correlated with insulin levels (r=0.40, p<0.001 in this study) were stratified. Again, no departure from random expectation was observed in any subgroup.

D. Discussion.

These results demonstrate an absence of linkage between the ACE/hGH loci and hypertension in this population. This study had substantial power to detect linkage, analyzing a large number of 30 hypertensive sib pairs and using an extremely polymorphic marker that displays no recombination with ACE. The lack of departure from random segregation of the marker locus and hypertension, together with the absence of linkage disequilibrium between ACE and hGH markers and hyper tension, exclude the hypothesis that common variants at this locus could have a significant effect on blood pressure. The analyses of more homogeneous subsets of hypertensive pairs potentially enriched for a genetic component were also negative, though the 95% confidence limits on those subject remain large. These results do not rule out the possibility that rare mutation of the ACE gene could, like LDL-receptor mutations in hypercholesterolemia (Goldstein et al., 1979), have a significant effect on the trait but account for only a small percentage of affected individuals in the population. Thus, no association was found between ACE and hypertension.

EXAMPLE 7

Linkage Analysis Between AGT and Hypertension

The analysis of linkage between AGT and hypertension was carried out using the methods described above in Example 4. Three distinct steps were utilized in the analytical approach to identify and confirm a linkage between the AGT gene and hypertension: (1) a genetic linkage study; (2) an identification of molecular variants of AGT followed by a comparison of their frequencies in hypertensive cases and controls; and (3) an analysis of variance of plasma angiotensinogen concentration in hypertensive subjects as a function of AGT genotypes. When parental alleles at a marker locus can be identified unambiguously in their offspring, the observed proportion of sibling pairs sharing 0, 1 or 2 alleles i.b.d. can be directly compared to the expected proportions of ¼, ½, and ¼ under the hypothesis of no genetic linkage. For a disease of late onset, however, parents are usually not available for sampling. Furthermore, even for a marker with multiple alleles and high heterozygosity, the identity by state (i.b.s.) of two alleles in a pair of siblings does not imply that they are identical by descent, that is, inherited from the same parental gene: this allele may have been present in more than one of the four parental genes. In such cases, one must express the probability that two alleles in the offspring be identical by state as a function of Mendelian transmission rules and allelic frequencies in the reference population. The mean number of alleles shared by siblings is then compared to the value expected under assumption of independent segregation of hypertension and marker through a one-sided Student-test (Blackwelder et al., 1985; Lange, 1986).

After molecular variants of AGT were identified, their frequencies in cases and controls were directly compared. The subject in each hypertensive sibship with lowest identification number was selected as the index case; the panel of control subjects consisted of a sample of healthy, unrelated individuals from the same population. Lastly, effect of AGT genotypes on plasma angiotensinogen was tested by analysis of variance of all hypertensive subjects for which a measurement was available, taking into account gender or population of origin as an independent, fixed effect.

A. Genetic Linkage Between AGT and Essential Hypertension.

A total of 215 sibships were collected at two centers under separate sampling procedures. The Salt Lake City sample consisted of 132 sibships, each with at least two hypertensive siblings on antihypertensive medication, which had been ascertained directly from the local population. In Paris, patients from 83 families had been selected in a hypertension clinic on the basis of strict criteria with respect to blood pressure and body-mass index. The impact of the difference in ascertainment protocols is reflected in the summary statistics presented in Table 3. A highly informative genetic marker at the AGT locus, based on a variable tandem repeat of the sequence motif GT (Kotelevstev et al., 1991), was characterized in all study subjects; reference frequencies and genotypes were determined and are set forth in U.S. Pat. No. 5,763,168. Because of anticipated etiological heterogeneity of this disease, analyses were performed not only on total samples, but also on predefined subsets of the data which had the potential of exhibiting greater genetic homogeneity, such as subjects with earlier onset or with more severe hypertension (Jeunemaitre et al., 1992a, 1992b). Linkage did not reach significance in the total sample from Salt Lake City ($t=1.22$, $p=0.11$). However, a 7.7% excess of alleles shared by hypertensive siblings was observed in the total sample from Paris ($t=1.71$, $p$-$<0.05$), and a slightly greater level of significance was achieved when both samples were pooled ($t=2.02$, $p=0.02$, Table 4). Similar results were observed when only subjects with earlier onset of hypertension were considered (Table 5). By contrast, a more significant, 15% to 18% excess of alleles shared by the sibling pairs was observed when analysis was restricted to patients with "more severe" hypertension, predefined in both groups as subjects requiring two medications for blood pressure control or with diastolic blood pressure equal to or greater than 100 mmHg (Table 5). In addition to the greater significance achieved by pooling the "more severe" hypertensive pairs from both studies ($t=3.40$, $p<0.001$), the replication of this finding in two different hypertensive populations is of critical relevance in evaluating this statistical evidence (Study, Salt Lake City).

Because estrogens stimulate angiotensinogen production (Cain et al., 1971; Menard et al., 1973), the data were partitioned by gender (Table 6). In the Salt Lake City samples, as well as in the Paris samples, linkage remained significant among male-male pairs only ($t=2.42$, $p<0.01$, samples pooled). Furthermore, the 37 male-male pairs from both samples who also met the criteria for 'more severe' hypertension exhibited a 33% excess of shared alleles ($t=3.60$, $p<0.001$). Forty-eight women in the Salt Lake City sample were taking synthetic estrogens or oral preparations containing natural estrogens, while none in the Paris sample were doing so; still, there was no excess of shared alleles among the 35 Utah female pairs who were not taking exogenous estrogens.

TABLE 4

Sib Pair Linkage Analysis at the Angiotensinogen Locus in Salt Lake City and Paris

| Study | Sibships n | Pairs n | Alleles Shared Observed/Expected | Excess | Significance t | p |
|---|---|---|---|---|---|---|
| Salt Lake City | | | | | | |
| Pairs | 102 | 102 | 132/126.9 | | | |
| Trios | 20 | 60 | 85/74.7 | | | |
| Quartets | 7 | 42 | 56/52.3 | | | |
| Quintet | 1 | 10 | 8/12.4 | | | |
| Sextets | 2 | 32 | 31/37.3 | | | |
| Total | 132 | 244 | 312/303.6 | 3.8% | 1.22 | 0.11 |
| Paris | | | | | | |
| Paris | 62 | 62 | 86/74.4 | | | |
| Trios | 19 | 57 | 71/70.7 | | | |
| Quartets | 1 | 6 | 9/7.5 | | | |
| Quintet | 1 | 10 | 8/10 | | | |
| Sextets | 83 | 136 | 175/162.5 | 7.7% | 1.71 | <.05 |
| Total | 215 | 379 | 487/466.2 | 5.1% | 2.02 | 0.02 |

For each sample, the following is reported: the number of sibships and sibling pairs analyzed, the observed and expected number of alleles shared by the siblings for each sibship size, and the excess of alleles shared (%) after weighting by sibship size.

TABLE 5

Genetic Linkage in Sib Pairs Selected for Early Onset or More Severe Hypertension

| | Pairs n | Alleles Shared (observed/expected) | Excess | t | p |
|---|---|---|---|---|---|
| Age Dx <45 yrs | | | | | |
| Salt Lake City | 110 | 143/136.9 | 7.1% | 1.51 | p = 0.07 |
| Paris | 61 | 80/71.6 | 11.6% | 1.68 | p < 0.05 |
| TOTAL | 171 | 223/208.5 | 8.6% | 2.23 | p < 0.02 |
| Rx ≦2 drug or DBP ≧100 mmHg | | | | | |
| Salt Lake City | 50 | 74/62.3 | 18.0% | 2.58 | p < 0.01 |
| Paris | 60 | 85/72.9 | 15.3% | 2.25 | p < 0.02 |
| TOTAL | 110 | 159/136.2 | 17.1% | 3.40 | p < 0.001 |

TABLE 6

Genetic Linkage in Hypertensive Sib Pairs of Same Gender

| | Pairs n | Alleles Shared (observed/expected) | Excess | t | p |
|---|---|---|---|---|---|
| Male-Male Pairs | | | | | |
| Salt Lake City | 60 | 81/74.6 | 11.0% | 1.70 | p < 0.05 |
| Paris | 37 | 52/44.4 | 15.4% | 1.76 | p < 0.05 |
| TOTAL | 97 | 133/118.0 | 12.7% | 2.42 | p < 0.01 |
| Female-Female Pairs | | | | | |
| Salt Lake City | 79 | 96/98.3 | <2.3% | <0 | |
| Paris | 36 | 45/43.7 | 1.4% | 0.31 | p = 0.38 |
| TOTAL | 115 | 139/142.0 | <1.2% | <0 | |

B. Association Between Hypertension and Molecular Variants of AGT.

Observation of significant genetic linkage between essential hypertension and a marker at the AGT locus suggested that molecular variants in this gene might be causally implicated in the pathogenesis of essential hypertension. A direct search for such variants in all exons and in a 682-bp segment of the 5' noncoding region of AGT was performed on a sample consisting of the index cases of the more severely hypertensive pairs from both populations. Variants detected by electrophoresis of enzymatically amplified DNA segments under nondenaturing conditions (Orita, 1989) were submitted to direct DNA sequencing (Hata et al., 1990; U.S. Pat. No. 5,763,168). At least 15 distinct molecular variants have been identified, including five nucleotide substitutions in the 5' region of the gene, and 10 silent and missense variants (U.S. Pat. No. 5,763,168; Table 2). No variants have been detected within the N terminal portion of exon 2 that encode the site cleaved by renin.

The prevalence of each identified variant was compared between hypertensive index cases and control subjects. For the Salt Lake City sample, the first variant detected, M235T (a change from methionine to threonine at amino acid 235 of AGT), was significantly more frequent in all hypertensive index cases than in controls, with a further increase in frequency among the more severely affected index cases (Table 7). These results were replicated in the Paris sample. The association was significant in either sex. In particular, M235T was significantly more prevalent among female hypertensives (0.51) than in controls (0.37) ($X_1^2=16.9$, p<0.001).

frequencies of these haplotypes were contrasted among hypertensives and control subjects, haplotypes carrying M235T, with or without T174M, were observed more often among all hypertensive index cases (0.14 and 0.33, n=215) than in controls (0.09 and 0.28, n=232), both differences being significant ($X_1^2=5.6$, p<0.02 and 13.5, p<0.01).

TABLE 7

Linkage Disequilibrium Between Controls and Hypertensives

|  |  | T174M |  | M235T |  |
|---|---|---|---|---|---|
|  | n | q | $\chi_1^2$ | q | $\chi_1^2$ |
| Salt Lake City |  |  |  |  |  |
| Controls | 280 | .08 |  | .35 |  |
| All Probands | 264 | .12 | 2.8, ns | .44 | 4.5, p < 0.05 |
| More Severe Probands | 72 | .19 | 8.4, p < 0.01 | .49 | 4.5, p < 0.05 |
| Paris |  |  |  |  |  |
| Controls | 184 | .09 |  | .38 |  |
| All Probands | 166 | .18 | 5.9, p < 0.02 | .52 | 6.7, p < 0.01 |
| More Severe Probands | 88 | .19 | 5.5, p < 0.02 | .52 | 4.2, p < 0.05 |
| TOTAL |  |  |  |  |  |
| Controls | 464 | .09 |  | .36 |  |
| All Probands | 430 | .14 | 5.3, p < 0.05 | .47 | 11.1, p < 0.001 |
| (males/females) | (224/206) | (.16/.13) |  | (.44/.51) |  |
| More Severe Probands | 160 | .17 | 7.4, p < 0.01 | .51 | 11.6, p < 0.001 |
| (males/females) | (96/94) | (.14/.21) |  | (.45/.59) |  |

In each group are indicated the number of alleles analyzed (n), the allele frequency (g), and the significance of the association between controls and hypertensives calculated with a Chi square 1 d.f.
All Probands refers to the index hypertensive subjects of each sibship (n = 132, Salt Lake City; n = 83, Paris);
More Severe Probands refers to the index subjects of the more severely affected pairs.
There was no significant difference in M235T and T174M allelic frequencies between males and females.
No departure from Hardy-Weinberg equilibrium was observed in repartition of these genotypes.

In each group are indicated the number of alleles analyzed (n), the allele frequency (q), and the significance of the association between controls and hypertensives calculated with a Chi square 1 d.f All probands refers to the index hypertensive subjects of each sibship (n=132, Salt Lake City; n=83, Paris); more severe probands refers to the index subjects of the more severely affected pairs. There was no significant difference in M235T and T174M allelic frequencies between males and females. No departure from Hardy-Weinberg equilibrium was observed in repartition of these genotypes.

Of the other variants tested, only T174M also displayed significant association in both samples (Table 7). Analysis of the distribution of M235T and T174M genotypes indicates that these two variants were in complete linkage disequilibrium ($X_6^2=36.4$, p<0.0001): T174M was present in a subset of chromosomes carrying the M235T allele. When the C. Association with Plasma Concentrations of Angiotensinogen.

A possible relationship between plasma concentrations of angiotensinogen and two molecular variants of this protein (M235T and T174M) was tested by analysis of variance, as a function of genotype and gender, in hypertensive subjects in each sample. Women taking oral preparations of estrogens were excluded from this analysis. No significant differences were observed when subjects were classified according to genotype at residue 174. By contrast, plasma concentrations of angiotensinogen were significantly higher in women carrying the M235T variant in each population sample; when both samples were jointly considered in an analysis of variance taking into account gender and population as fixed effects, genotypic differences were highly significant (F2313=14.9, p<0.0001) (Table 8).

TABLE 8

Influence of the M235T Variant on Plasma Angiotensinogen Concentrations

| M235T | AA | Aa | aa | Significance: F, p |
|---|---|---|---|---|
| Salt Lake City | 1422 ± 247 (67) | 1479 ± 311 (109) | 1641 ± 407 (33)[1,2] | 5.92, p < 0.005[3] |
| Males | 1376 ± 247 (42) | 1404 ± 265 (59) | 1499 ± 207 (18) | 1.53, ns |
| Females | 1500 ± 232 (25) | 1566 ± 340 (50) | 1811 ± 519 (15)[1,2] | 3.91, p < 0.02 |
| Paris | 1085 ± 210 (32) | 1318 ± 383 (55)[4] | 1514 ± 511 (29)[1,2] | 7.90, p < 0.001[3] |
| Males | 1086 ± 244 (17) | 1311 ± 290 (26)[4] | 1377 ± 606 (10)[1] | 2.82, p = 0.07 |
| Females | 1084 ± 173 (15) | 1324 ± 456 (29)[4] | 1586 ± 455 (19)[1,2] | 6.44, p < 0.01 |

TABLE 8-continued

Influence of the M235T Variant on Plasma Angiotensinogen Concentrations

| M235T | AA | Aa | aa | Significance: F, p |
|---|---|---|---|---|
| TOTAL | 1313 ± 283 (99) | 1425 ± 344 (164) | 1582 ± 459 (62)[1,2] | 14.90, p < 0.0001[5] |
| Males | 1293 ± 277 (59) | 1375 ± 274 (85) | 1456 ± 391 (28)[2] | 3.10, p < 0.05 |
| Females | 1344 ± 292 (40) | 1477 ± 401 (79) | 1685 ± 490 (34)[1,2] | 6.82, p < 0.001 |

Plasma angiotensinogen concentrations are expressed as mean ± 1 S.D. (ng/ml).
A: allele M235;
a: allele 235T.
The statistical significance tested by one-way analysis of variance is unmarked.
[1]p < 0.05 between heterozygotes and homozygotes M235.
[2]p < 0.05 between homozygotes M235T and homozygotes M235.
[3]The statistical significance tested by two-way analysis of variance with gender as a fixed effect.
[4]p < 0.05 between homozygotes M235T and heterozygotes.
[5]The statistical significance tested by three-way analysis of variance with gender and population as fixed effects.

The effect associated with M235T appeared to be codominant in females. Higher concentrations were found in females than males in Salt Lake City (t=4.3, p<0.001) but not in Paris (t=1.41, p=0.16). While the effect of estrogens on angiotensinogen production may account for the gender difference noted in Salt Lake City, a difference in mean values between the two samples is less likely to be of physiological significance; all subjects belonging to a given population sample were assayed concurrently and referred to the same standard, but measurements for Salt Lake City and Paris samples were performed six months apart, using different preparations of renin and different standards.

D. Analysis of the G-6A Vanant.

The data detailed above contained insufficient evidence concerning the G-6A variant which led to the interpretation that the G-6A variant occurred only in total association with A-20C variant. Thus, in Table 2, it was reported that the frequency of the genes carrying both A-20C and G-6A variants was 14% in Utah Controls (C) and 19% in Utah Hypertensives (H). The frequency was 18% in French hypertensives, with no testing performed in French controls. The frequency of the M235T variant was 36% and 38% in Utah and French controls, respectively. While this data is correct, it did not take into consideration the fact that the G-6A variant could also occur on genes which did not carry the A-20C variant. Studies were conducted in Japanese and Utah populations and analyzed as described above. In tests involving 107 random Caucasian controls from Utah and 99 random Japanese individuals, the G-6A variant was seen in over 90% of the Caucasian genes carrying M235T and in 98% of the corresponding Japanese genes. The G-6A variant was seen in only one Caucasian gene carrying the native M235 gene. See Table 9. Thus, more than 90% of the Utah hypertensives carying M235T also carry G-6A, rather than the 40% suggested in Table 2.

TABLE 9

Frequencies of AGT Haplotypes in Caucasian and Japanese Controls

| Haplotype | Caucasians | Japanese |
|---|---|---|
| M235,[1] G (-6)[1] | 0.067 | 0.242 |
| M235, A (-6) | 0.005 | 0.000 |
| T235, G (-6) | 0.038 | 0.015 |
| T235, A (-6) | 0.350 | 0.743 |
| Total | 1.000 | 1.000 |

[1]The wild-type sequence at these positions

E. Discussion

Three sets of observations—genetic linkage, allelic associations, and differences in plasma angiotensinogen concentrations among AGT genotypes—in two independent samples of hypertensive subjects establishes involvement of angiotensinogen in the pathogenesis of essential hypertension.

1. Genetic Linkage in Hypertensive Siblings.

Genetic linkage was inferred through the application of first principles of Mendelian genetics to pairs of related individuals (Blackwelder et al., 1985), an approach requiring a large number of affected pairs and a highly polymorphic marker at the test locus (Risch, 1990; Bishop et al., 1990). This study design is well suited to common disorders where the anticipated multiplicity and heterogeneity of causal factors defies conventional approaches that rely on explicit formulation of a model of inheritance. In the Utah sample, significant linkage was achieved only for the subset of more severely affected subjects—as defined by the use of two antihypertensive drugs or by a diastolic blood pressure equal to or greater than 100 mmHg; by contrast, linkage reached significance in the total sample in Paris. This observation most likely reflects the different ascertainment schemes applied in each study. Salt Lake City sibships represent a population-based collection of hypertensive subjects, whereas subjects in Paris were recruited through referral to a hypertension clinic and with the application of strict exclusion criteria (see Example 1). The former sample has the merit of being population-based; however, the inclusion of less severely affected subjects, as reflected by lower treated blood pressure values than in the French sample, may have led to the appearance of greater etiological heterogeneity in the total sample.

2. Association Between Hypertension and Molecular Variants of AGT.

Genetic linkage indicated that variants of AGT could be involved in the pathogenesis of essential hypertension. Among the 15 molecular variants of the AGT gene identified, significant association with hypertension was observed for two distinct amino acid substitutions, M235T and T174M. The significance of this association was established by contrasting allelic frequencies in hypertensive and control subjects. Although this design is liable to bias due to uncontrolled stratification, three arguments support the interpretation that the observed associations are not spurious: (1) significance is obtained in independent samples from two different populations; (2) gene frequencies are remarkably similar in these two samples, suggesting that little variation should be anticipated among Caucasians of Northern and Western European descent; (3) no differences in allelic frequencies among these hypertensive and control groups have been observed at other loci including renin, angiotensin converting enzyme and hGH (Examples 5 and 6).

Variants M235T and T174M exhibited complete linkage disequilibrium, as T174M occurred on a subset of the haplotypes carrying the M23ST variant, and both haplotypes were observed at higher frequency among hypertensives. Several interpretations can be proposed to account for this observation: (1) M235T directly mediates a predisposition to hypertension; (2) an unidentified risk factor is common to both haplotypes; (3) each haplotype harbors a distinct risk factor.

Although both variants were found significantly more often in female hypertensives than in control subjects, no linkage was evident among pairs of female hypertensives in either sample. These observations could be reconciled by postulating that angiotensinogen contributes to hypertensive risk directly in males but indirectly in females, where another estrogen-modulated factor may mediate the impact of the angiotensinogen-associated predisposition; documented differences in the effects of testosterone and estrogens on the regulation of genes of the renin-angiotensin system support this hypothesis (Bachmann et al., 1991). While it is conceivable that the predispositions identified by linkage and by association represent independent variants, the parallel increase of both association and linkage in subsets of the data suggests that they are two manifestations of the same genetic determinant.

In addition to the significant association with hypertension initially noted for M235T and T174M variants, analysis of the G-6A variant shows this variant is also significantly associated with hypertension. The very strong association observed between M235T and G-6A has two important implications: (1) all associations noted between M235T and hypertension extend directly to G-6A, that is, G-6A is also diagnostic of a predisposition to hypertension; (2) it is unlikely that statistical tests alone can resolve the relative merit of either one as a marker for this predisposition, as it would require much greater sample sizes than those analyzed so far. These new observations now dictate four alternative interpretations of the data (instead of the former two): (1) M235T and G-6A both serve as markers for a predisposition to the development of hypertension encoded by yet another, unknown molecular variant; (2) M235T is causally involved while G-6A is a passive "hitchhiker"; (3) G-6A is causally involved, M235T being the passive "hitchhiker"; or (4) both M235T and G-6A are causal; each contributes a difference in the function of the angiotensinogen gene and protein Regardless of which interpretation may be correct, the data clearly demonstrates the significant association of each variant with hypertension and the ability of both two variants to be an indicator of predisposition to hypertension.

In view of these findings, molecular variants of the angiotensinogen gene constitute an inherited predisposition to essential hypertension in humans.

EXAMPLE 8

Screening for AGT Variants

Healthy subjects and pregnant women were screened for the M235T variant using PCR amplification and allele-specific oligonucleotide hybridization as described in Example 4. It was found that healthy subjects who carried the M235T variant had plasma levels of angiotensinogen higher than in non-carriers, and also had higher blood pressure. Both of these differences were found to be statistically significant. It was also found that the variant was not limited to Caucausians. The M235T variant was found to be significantly increased in women presenting preeclampsia during pregnancy.

EXAMPLE 9

Haplotypes of Angiotensinogen in Essential Hypertension

A. Subjects and Methods

1. Study Subjects.

The grandparents of the Utah families included in the CEPH database were used as controls for the frequency of the AGT diallelic polymorphisms and to define the corresponding haplotypes. French hypertensive patients were selected from the HYPERGENE data set of hypertensive families recruited in the Broussais Hypertension Clinic in Paris (Charru et al., 1994). Only the 477 probands (age 49.4±8.4 years; 48% men) who satisfied the following main criteria were considered: Caucasian origin, hypertension established on the basis of diastolic BP $\geq$95 mmHg and for the presence of an antihypertensive treatment mean BP 158.9±22.6/98.8±133,3 mmHg; 73% on treatment), onset of hypertension at <55 years of age (40.3±10.8 years), and body-mass index >27 kg/m$^2$ (25.4±3.8), The absence of secondary hypertension was established by an extensive inpatient workup when the latter was clinically indicated. The absence of diabetes mellitus (mean blood glucose 5.4±0.7 mmol/liter) was assessed by the presence of the following three criteria: (1) the absence of personal diagnosis of diabetes meffitus, (2) the absence of antidiabetic drug treatment, and (3) a fasting blood-glucose level <6.5 mmol/liter. Also, patients were not eligible when other factors that could affect BP—for example, renal insufficiency (mean plasma creatinine 85.8±22.4 μmol/liter), excessive alcohol consumption, and estrogen use—were present.

Among these 477 probands of hypertensive families, 75 probands already had been studied in our previous analysis (Jeunemaitre et al., 1992c). The clinical and biological characteristics of these 75 probands were not statistically different from those of the other 402 probands. They were not excluded from this analysis in order to keep the maximal power of the haplotype analysis.

French normotensive patients were selected by the Institute Regional pour la Sante (IRSA) during an annual medical visit for preventive medicine. All of the 364 individuals analyzed were Caucasians and were recruited in two main centers of the regions Centre and Picardie, which are located ~200 km south and north, respectively, of Paris. This control group was different from that analyzed in our previous study (Jeunemaitre et al., 1992c). Normotensive individuals were selected to match the distributions of age (46.1±7.6 years), gender (445 men), and body mass index (23.6±2.2 kg/mg$^2$) observed in the hypertensive subjects. All had sitting systolic and diastolic BP<140 and <90 mmHg (mean BP 113.8±9.4/71.4±6.5 mmHg), respectively, without any history of hypertension or antihypertensive treatment, diabetes mellitus (mean blood glucose 5.02±0.5 mmo/liter), renal insufficiency (mean plasma creatmine 71.6±12.2 μmol/liter), or cardiovascular disease and without family history (in parents and siblings) of hypertension.

Japanese hypertensives and controls have been described elsewhere (Hata et al. 1994). Patients had established hypertension (systolic BP>160 mmHg and/or diastolic BP>90 mmHg), in the absence of any secondary cause, diabetes, or renal disease. All patients and controls were ascertained at Yamanishi University Hospital.

Several segments of the 3' region of the human AGT gene have been shown to contain sequences involved in the cell type-dependent activation of the gene (Nibu et al., 1994a, 1994b). A systematic search was performed by SSCP analysis on the region containing an enhancer core element from +2170 to +2230, using the primers indicated in Table 10 and three different nondenaturing conditions. This systematic search was done in 20 M235M homozygous and 20 T235T homozygous French individuals. No electrophoretic variant was observed. In addition, direct sequencing also was performed in 16 individuals, all homozygous for the T235 allele, for the 5' region of the gene (from nucleotide −800 to nucleotide −1), the five exons, and the entire untranslated region of the gene.

TABLE 10

Primers Used for Detection of Mutations in 5' Region of AGT Gene by SSCP Analysis

| Location | Forward Primer | | Reverse Primer | |
| --- | --- | --- | --- | --- |
| −1221 to −1004 | AGACAAGTGATTTTTGAGGAGTC | (SEQ ID NO:23) | AACAACAAAGAGCAGGAAGAGATGG | (SEQ ID NO:24) |
| −1049 to −797 | CTTCTGCCTCATATCCAGGC | (SEQ ID NO:25) | ACCTTGGTGAGAGTCGCCAG | (SEQ ID NO:26) |
| −867 to −656 | ATCACCACTCCCAACCTGCC | (SEQ ID NO:27) | ATGCCTTCAGGATGCAGGCA | (SEQ ID NO:28) |
| −706 to −456 | ACATTTGCAATTTGTACAGC | (SEQ ID NO:29) | GCCCGCTCATGGGATGTG | (SEQ ID NO:30) |
| −421 to −171 | AAGACTCTCTCCCCTGCCCTC | (SEQ ID NO:31) | GAAGTCTTAGTGATCGATGCAG | (SEQ ID NO:32) |
| −164 to +73 | AGAGGTCCCAGCGTGAGTGT | (SEQ ID NO:33) | AGACCAGAAGGAGCTGAGGG | (SEQ ID NO:34) |
| +2141 to +2258 | ACAGATGTATACAATTCAGCAG | (SEQ ID NO:35) | CACCTAAAACTTCAAAGGACTG | (SEQ ID NO:36) |

2. Identification of Polyorphisms.

a. Search for new diallelic polymorphisms. An initial search for polymorphisms (Jeunemaitre et al., 1992c), relying on conformational variation in electrophoresis under nondenaturing conditions (Orita et al., 1989), spanned all coding segments of exons and splice junctions. In addition to the M235T and T174M missense mutations, four other polymorphisms, at positions −532, −20, −18, and −6 upstream of the transcription start site, and a polymorphism in intron 3, at position −13 relative to the beginning of exon 4, had been detected. With the same methodology, this search was extended to nucleotide −1221 upstream of the gene, in a panel of 96 French hypertensive subjects.

Each sample was electrophoresed under at least two conditions: (1) a 0.5×Hydrolink™ MDE™ (AT Biochem) prepared in 0.6×TBE (1×TBE=90 mM Tris-borate [pH 7.8], 2 mM EDTA), run at room temperature at 400 V for 14–20 h; and (2) a 5% polyacrylamide gel (49:1 polyacrylamide:methylene-bis acrylamide) prepared in 0.5× THE, run at +4° C. at 15 W constant power for 3–4 h. Direct sequencing of electrophoretic variants was performed as described elsewhere (Jeunemaitre et al., 1992c).

b. Genotyping. The frequency of each variant was established in cases and controls by allele-specific oligonucleotide hybridization using the methodology described elsewhere (Jeunemaitre et al., 1992c) and the primers indicated in Table 11. The G-6A variant could not be resolved by this technique without ambiguity, probably because of the high GC content of that sequence. For the G-6A variant, the mutagenically separated PCR technique, in which both normal and mutant alleles are amplified in the same tube, using different length allele-specific primers (Rust et al., 1993) was used. The following primers were designed with one forward primer and two reverse primers in which additional deliberate differences (underlined) were introduced to correspond to the molecular variant and to reduce cross-reactions between the two alleles:

FP-6, 5'-GTGTCGACTTCTGGCATCTGTCCTTCTGG-3' (SEQ ID NO:51)

RP-6A, 5'-TACCCAGAACAACGGCAGCTTCTTCCAC<u>T</u>-3' (SEQ ID NO:52); and

RP-6G, 5'-CCGGTTACCTTCTGCTGTAC<u>A</u>GCCCAGAACAACGGCAGCTTCTTCCA<u>TC</u>-3' (SEQ ID NO:53).

TABLE 11

Primers Used for Detection of ATG Polymorphisms by Specific Oligonucleotide Hybridization

| Location | Primer 1 | | Primer 2 | |
|---|---|---|---|---|
| -20 | ATAGGGCATCGTGAC | (SEQ ID NO:37) | ATAGGGCCTCGTGAC | (SEQ ID NO:38) |
| -532 | GTGTGTTTTCCCCAGT | (SEQ ID NO:39) | TGTGTGTTTTCCCAGT | (SEQ ID NO:40) |
| -776 | TGTTATAACGACTACAA | (SEQ ID NO:41) | TGTAGTCATTATAACAG | (SEQ ID NO:42) |
| -793 | AGGGCATGACAGAGAC | (SEQ ID NO:43) | GTCTCTATCATGCCCT | (SEQ ID NO:44) |
| -830 | GTCACTTGTGATCACTG | (SEQ ID NO:45) | GTCACTTGAGATCACTG | (SEQ ID NO:46) |
| -1074 | TGTTTGTTGATTGTTCA | (SEQ ID NO:47) | TGAACAATAAACAAACA | (SEQ ID NO:48) |
| Int 3 | ATCTCCCCAGGACCATC | (SEQ ID NO:49) | GATGGTCCTTGGGAGAT | (SEQ ID NO:50) |

PCR reactions were conducted in a 25-$\mu$l reaction volume containing 2.5 $\mu$l of 10×PCR buffer (500 mM KCl, 100 mM Tris HCl, pH 8.3, and 0.01% gelatine), 1.5 mM MgCl$_2$, 10 $\mu$M each of the four dNTPs, 10 pmol each of the three primers, and 0.5 units Taq polymerase. The first denaturation step (94° C. for 5 min) was followed by 35 cycles, each of 94° C. for 45 s, 62° C. for 45 s, and 72° C. for 45 s, and by a final extension at 72° C. for 7 min. The amplification reaction yields a 187-bp and a 207-bp product for the A-6 and G-6 alleles, respectively, which were resolved on a 2% agarose gel.

c. Statistical Analysis. Comparison of genotypic frequencies of single polymorphisms were performed by use of contingency $X^2$ tests. Pairwise linkage-disequilibrium coefficients were estimated by the maximum-likelihood method, and the extent of disequilibrium was expressed as the D'=D/D$_{max}$ or D/D$_{min}$, according to Thompson et al. (1988). Allelic or haplotypic frequencies for one or more loci were estimated by the maximum-likelihood method, by use of a simplified version of the computer program GENEF (J.-M. Lalouel, unpublished data). In analyses involving single codominant loci, this coincides with direct gene counting. Rather than estimating frequencies of a large number of unobserved haplotypes, however, we used a sequential inclusion procedure operating as follows: (1) after inclusion of the M235T polymorphism, additional polymorphisms were sequentially added one at a time; joint estimation of haplotypes yielded the minimum sets of haplotypes required to account for the observations, with all haplotypes below a frequency of ¼N, where N is the sample size, being automatically eliminated; (2) in five instances, a rare haplotype was required to account for only one possible observed genotype, and a parsimonious solution was obtained by deleting that rare genotype. The final set of haplotypes generated remained the same, whatever the order in which markers sequentially were added, and only five genotypes required unique, rare haplotypes and consequently were excluded.

Since most of the polymorphisms were in complete linkage disequilibrium with one another, this strategy led to nearly unambiguous haplotypes. Thus, instead of a global maximum-likelihood method that would have raised more df, statistical comparisons between cases and controls were performed by use of simple $X^2$ tests of homogeneity, with continuity correction.

B. Results

1. Diallelic Polymorphisms

Since a report on AGT variants, four additional variants have been detected, at positions -776, -793, -830, and -1074. None occurs in a region known, so far, to affect the expression of the AGT gene. No electrophoretic variant was found either in the 80 bp of exon 5 (+1399 to +1478) by SSCP analysis or in the entire untranslated 3' region by direct sequencing of 16 subjects homozygous for TT235.

The frequencies of seven polymorphisms located within 1 kb of the 5' region of the gene, the M235T and T174M variants in exon 2, and one polymorphism in intron 3 were analyzed in hypertensive and normotensive subjects (Table 12). The significantly higher frequency, in Japan, of T235 in hypertensive subjects compared with normotensive controls has been reported elsewhere (Hata et al., 1994). The study of French subjects confirmed the previously reported association (Jeunemaitre et al., 1992c) in another set of cases and controls (0.47 vs. 0.38, respectively; P=0.004). However, the frequency of the T174M variant was not significantly different between hypertensives and controls, whether from France or from Japan. A significant increase of the G-6A variant was observed in both groups, paralleling the difference observed for M235T. One other polymorphism, C-776T, displayed a significant difference between French hypertensives and controls (0.08 vs. 0.03, P=0.001), but that association was not replicated in the Japanese groups.

TABLE 12

Frequency of Angiotensinogen Polymorphisms in Hypertensives and Controls

| | Caucasians | | | Japanese | | |
|---|---|---|---|---|---|---|
| | Frequency | | | Frequency | | |
| Polymorphism | Hypertensives (n = 477) | Controls (n = 364) | $\chi_2^{2}$* | Hypertensives (n = 92) | Controls (n = 122) | $\chi_2^{2}$* |
| M235T | .465 | .379 | 12.1 (P = .004) | .913 | .762 | 17.4 (P = .002) |
| G-1074T | .124 | .091 | 4.8 (N.S.) | Not Tested | .147 | |
| T-830A | .067 | .060 | .8 (N.S.) | Not Tested | Not Tested | |
| G-793A | .127 | .092 | 8.6 (P = .01) | .179 | .153 | 3.8 (N.S.) |
| C-776T | .080 | .034 | 18.8 (P = .001) | .092 | .108 | 2.3 (N.S.) |
| C-532T | .122 | .094 | 4.7 (N.S.) | Not Tested | Not Tested | |
| A-20C | .160 | .175 | 1.0 (N.S.) | .225 | .195 | .7 (N.S.) |
| G-6A | .466 | .384 | 11.0 (P < .01) | .900 | .742 | 19.1 (P < .001) |
| T174M | .114 | .117 | 1.0 (N.S.) | .117 | .076 | 2.3 (N.S.) |
| A-13G (int3) | .082 | .069 | 1.8 (N.S.) | .376 | .287 | 5.0 (N.S.) |

*Test on genotype frequencies.
N.S. = Not Significant.

2. Pairwise Linkage Disequilibrium

The polymorphisms were typed in the entire set of Utah CEPH grandparents, in addition to the groups described above, and their patterns of linkage disequilibrium were examined. Most of the polymorphisms were in complete linkage disequilibrium with one another (Table 13).

The patterns of linkage disequilibrium analyzed in the CEPH group were in close agreement with those observed in French Caucasians. Despite strong ethnic differences in the frequency of the T235 allele, similar patterns of disequilibrium also were observed in the 122 normotensive Japanese.

TABLE 13

Pairwise Linkage-Disequilibrium Coefficients, Between AGT Gene Polymorphisms, Estimated in Caucasian Controls

| | ±D' * | | | | | | | | |
|---|---|---|---|---|---|---|---|---|---|
| Polymorphism | M235T | G-1074T | T-830A | G-793A | C-776T | C-532T | A-20C | G-6A | T174M |
| G-1074T | 1.00 | — | — | — | — | — | — | — | — |
| T-830A | −1.00 | −.75 | — | — | — | — | — | — | — |
| G-793A | 1.00 | 1.00 | −.51 | — | — | — | — | — | — |
| C-776T | 1.00 | .77 | 1.00 | .77 | — | — | — | — | — |
| C-532T | 1.00 | .96 | −.63 | .97 | 1.00 | — | — | — | — |
| A-20C | 1.00 | −1.00 | −1.00 | −1.00 | .57 | −1.00 | — | — | — |
| G-6A | .97 | 1.00 | −.76 | 1.00 | −1.00 | 1.00 | 1.00 | — | — |
| T174M | 1.00 | −1.00 | −1.00 | 1.00 | .40 | −1.00 | .94 | 1.00 | — |
| A-13G (int3) | .97 | −1.00 | .00 | 1.00 | .98 | −1.00 | −1.00 | .92 | −1.00 |

* All coefficients with absolute values >.70 significantly differ from 0 (P < $10^{-4}$).

In order to subdivide the T235 allele into frequent haplotypes, the linkage-disequilibrium patterns were summarized in terms of the allelic associations with either T235 or M235 (Table 14). The variants A-830 occurred only in genes carrying 235M. All other polymorphisms exhibited a quasi-complete linkage disequilibrium with M235T, each variant being only a subset of the T235 alleles. It is important to note that in both populations, the G-6A polymorphism was in complete linkage disequilibrium with M235T and occurred with the same frequency. Thus, the two polymorphisms almost always were seen together. As a result, although our subsequent analyses will refer primarily to M235T, all associations pertaining to the T235 allele extend directly to the A-6 polymorphism.

TABLE 14

Association Between Each Diallelic Angiotensinogen Polymorphism and T235 Allele

| Polymorphism and Sample (n) | | $P_i$* | $P_{ij}$** | $P_{j/i}$*** |
|---|---|---|---|---|
| M235T: | CEPH grandparents (152) | .388 | — | — |
| | French controls (364) | .380 | — | — |
| | Japanese controls (122) | .762 | | |

TABLE 14-continued

Association Between Each Diallelic Angiotensinogen Polymorphism and T235 Allele

| Polymorphism and Sample (n) | | $P_i$* | $P_{ij}$** | $P_{j/i}$*** |
|---|---|---|---|---|
| G-1074T: | CEPH grandparents (148) | .098 | .098 | 1.00 |
| | French controls (360) | .091 | .090 | .99 |
| | Japanese controls (122) | .153 | .153 | 1.00 |
| T-830A: | CEPH grandparents (139) | .090 | .000 | .00 |
| | French controls (344) | .060 | .000 | .00 |
| | Japanese controls (—) | — | — | — |

TABLE 14-continued

Association Between Each Diallelic Angiotensinogen
Polymorphism and T235 Allele

| Polymorphism and Sample (n) | | $P_i$* | $P_{ij}$** | $P_{j/i}$*** |
|---|---|---|---|---|
| G-793A: | CEPH grandparents (138) | .098 | .081 | .83 |
| | French controls (343) | .092 | .092 | 1.00 |
| | Japanese controls (122) | .147 | .143 | .97 |
| C-776T: | CEPH grandparents (137) | .048 | .037 | .76 |
| | French controls (338) | .034 | .034 | 1.00 |
| | Japanese controls (114) | .110 | .110 | 1.00 |
| C-532T: | CEPH grandparents (142) | .106 | .106 | 1.00 |
| | French controls (277) | .094 | .091 | .97 |
| | Japanese controls (—) | — | — | — |
| A-20C: | CEPH grandparents (144) | .135 | .135 | 1.00 |
| | French controls (339) | .177 | .177 | 1.00 |
| | Japanese controls (108) | .185 | .185 | 1.00 |
| G-6A: | CEPH grandparents (145) | .369 | .362 | .98 |
| | French controls (364) | .386 | .376 | .97 |
| | Japanese controls (113) | .743 | .739 | .99 |
| T-174M: | CEPH grandparents (138) | .101 | .101 | 1.00 |
| | French controls (355) | .117 | .117 | 1.00 |
| | Japanese controls (122) | .078 | .078 | 1.00 |
| A-13G (int3): | CEPH grandparents (146) | .079 | .079 | 1.00 |
| | French controls (362) | .069 | .067 | .97 |
| | Japanese controls (120) | .296 | .296 | 1.00 |

*Frequency of variant i.
**Joint Frequency of variant i and T235.
***Conditional probability that a gene carries T235, given that it carries i.

3. Multisite Haplotypes.

The distribution of the T235-associated polymorphisms into multisite haplotypes was examined first in the CEPH sample. For the purpose of the present study—that is, testing of the homogeneity of T235 haplotypes with respect to risk of hypertension—we sought to conserve df by generating a parsimonious set of haplotypes involving as many site polymorphisms as could be achieved. Although there is no formal, optimal solution to this problem, the observed patterns of multiway linkage disequilibrium yielded a rather straightforward solution. Variants at sites −1074, −793, and −532, with a few exceptions, always occurred together; only site −793 was considered in further analyses.

Sequential addition of site polymorphisms, independently of the sequence used for their incorporation, led invariably to a parsimonious set of five common haplotypes of T235, defined by five site polymorphisms (Table 15). In the CEPH sample, these five sites account for 233 of 238 haplotypes tested at all sites. Only five genotypes required unique, rare haplotypes and, consequently, were excluded. Inclusion of the A-13G(Int3) polymorphism would have required retention of multiple rare haplotypes or deletion of multiple T235 genes. To conserve power and df, this polymorphism was not included in subsequent analyses. The final set of haplotypes generated remained the same, whatever the order in which markers were added sequentially. Because of the very similar linkage disequilibrium in both populations between M235T and the other diallelic polymorphisms, the same haplotypes were generated in both the Caucasian group and the Japanese group.

TABLE 15

Angiotensinogen Haplotypes

| Haplotype * | Status of Allele ** | | | | |
|---|---|---|---|---|---|
| | T235 | M174 | T-776 | A-793 | C-20 |
| H1 | − | − | − | − | − |
| H2 | + | − | − | − | − |
| H3 | + | − | + | − | − |
| H4 | + | − | − | + | − |
| H5 | + | − | − | − | + |
| H6 | + | + | − | − | + |

* Only informative haplotypes have been mentioned.
** A plus sign (+) denotes presence of allele; a minus sign (−) denotes absence of allele.

4. Testing Haplotypes in Hypertensives and Normotensives.

The estimated frequencies of the six haplotypes identified above were compared, between hypertensive and controls, in both the French Caucasian population and the Japanese population (Table 16). The strong and significant increase of H1 in normotensives that was observed in both populations simply reflects the symmetrical decrease of the T235 allele, a decrease already observed in the single-locus analysis.

In Caucasians, the difference in H1 frequency (0.093, P<0.001) was explained mainly by two haplotypes: H3 (T235/T776) and H4 (T235/A-793). This pattern was not observed in Japanese, where most of the haplotypes subdividing T235 displayed a small difference between hypertensives and controls. In this group, the only marginal significant difference was observed for the T235 haplotype not bearing any other polymorphism (i.e., H2; see Table 16).

TABLE 16

Haplotype Frequencies in Hypertensives and Controls

| | Caucasians | | | Japanese | | |
|---|---|---|---|---|---|---|
| | Frequency | | | Frequency | | |
| Haplotype | Hypertensives (n = 914) | Controls (n = 644) | $\chi_1^2$ | Hypertensives (n = 176) | Controls (n = 198) | $\chi_1^2$ |
| H1: M235 | .540 | .633 | 13.88 (P < .001) | .091 | .242 | 15.08 (P < .001) |
| H2: T235 | .101 | .079 | 2.32 | .426 | .328 | 3.81 (P < .05) |
| H3: T235 + T-776 | .073 | .031 | 12.78 (P < .001) | .074 | .101 | .85 |
| H4: T235 + A-793 | .124 | .085 | 6.03 (P < .01) | .182 | .146 | .85 |
| H5: T235 + C-20 | .048 | .053 | .16 | .131 | .101 | .81 |
| H6: T235 + M174 + C-20 | .109 | .118 | .77 | .097 | .081 | .29 |

5. Distribution of the GT Aleles

In order to investigate the possibility of an association between a multiallelic series of alleles at this locus and hypertension, alleles of the microsatellite dinucleotide (GT) repeat at the angiotensinogen locus (Kotelevstev et al., 1991) were examined in all samples. The frequencies observed in Utah CEPH subjects were very similar to those exhibited by French controls. To reduce df, alleles at either end of the distribution were pooled. A significant difference was observed between normotensive and hypertensive Caucasian subjects ($X^2$[7 df]=21.56, P<0.01). The decrease in $(GT)_{16}$ in hypertensives compared with normotensives (0.358 vs. 0.416) accounted for most of this statistical difference. As a consequence, a slight increase was detected in the other alleles, but no particular shift from one to another could be observed.

A different pattern was observed in the Japanese. Compared with that observed in Caucasians, the distribution was shifted toward shorter and longer alleles, the $(GT)_{16}$ allele accounting only for 11.4% and 8.9% of the alleles in controls and hypertensives, respectively. When all the alleles were analyzed, a marginally significant difference was observed between normotensive and hypertensive Japanese ($X^{2[7}$ df]=14.1, P<0.05). A tendency toward longer alleles was observed in hypertensives, significant when the overall distribution was partitioned into two groups, one group more than and the other group equal to or less than the $(GT)_{17}$ ($X^2$[1 df]=8.76, P<0.004).

6. Conditional Distributions of the GT Alleles According to Diallelic Polymorphisms.

Conditional distributions of the GT alleles, given other diallelic polymorphisms, were analyzed in the French and Japanese groups. Each individual variant showed a strong degree of association with GT alleles that was very similar in both populations and in hypertensive and normotensive subjects (data not shown). The highest associations were observed for M174, exhibiting 91% and 95% of $(GT)_{14}$ in French and Japanese, respectively, and for G(Int3), exhibiting 88% and 84% of $(GT)_{>20}$ in French and Japanese, respectively. Only the T(-776) variant showed a different pattern of linkage disequilibrium, mainly associated with $(GT)_{17}$ in French and with $(GT)_{\leq 13}$ in Japanese.

Since there was a significant association between T235 and hypertension, it was important to examine the conditional distributions of GT alleles within haplotypes carrying either M235 or T235. Whereas the distribution of the GT alleles for T235 was almost uniform, 65% of M235 genes exhibited allele $(GT)_{16}$ in CEPH individuals and French controls, as a consequence of the strong linkage disequilibrium between these two polymorphisms. In Japanese individuals, 38%, 21%, and 19% of M235 genes exhibited the $(GT)_{16}$, $(GT)_{17}$, and $(GT)_{13-14}$ alleles, respectively. These patterns of linkage disequilibrium also were observed in hypertensive individuals (data not shown).

7. The 235T/A-6 Allele—Ancestral Form of the AGT Genes

The associations between the different polymorphisms of the human AGT gene are summarized in Jeunemaitre et al. (1997). The broad, uniform distribution of GT alleles, as well as the presence of multiple site polymorphisms on haplotypes carrying both T235 and A-6, suggest that T235 and A-6 may mark the original form of the gene. This interpretation is supported further by the presence of this form of the gene in all primate species examined (Inoue et al., 1997).

The patterns of association exhibited by a number of diallelic polymorphisms suggest that molecular variants have arisen by mutation on ancestral genes carrying T235 and a particular GT allele. This pattern of genetic diversity suggests a development by spatial divergence in subdivided populations, rather than by temporal divergence in a homogeneous founder population. It is intriguing that the M235 variant, which occurs mainly on $(GT)_{16}$, is strongly associated also with the G-6 substitution. The persistence of this association may have arisen by chance, or it may represent a coordinated response to natural selection.

C. Discussion

Generation of haplotypes is a powerful method for testing the hypothesis that a specific allele mediates predisposition, and explains the observed association of the T235 allele with hypertension. Two types of genetic polymorphism can be applied to generate haplotypes: (1) diallelic polymorphisms resulting from point mutations, and (2) multiallelic variation associated with a variable number of simple-sequence-tandem repeats. Several arguments can be proposed in support of the use of a battery of diallelic series to partition T235 haplotypes. First, there is ample evidence that, on an evolutionary time scale, single nucleotide substitutions are much more stable than are simple-tandem-repeat sequences (Stallings et al., 1991). For a common risk factor, a multiallelic series may dissipate statistical power, through both the generation of a large number of df and the functional mutation into a number of marker alleles (Hyer et al., 1991). Second, several arguments support the hypothesis that the T235 allele marks the original form of the gene and that M235 is the neomorph: (1) the strong linkage disequilibrium between M235 and one of the alleles of the AGT microsatellite marker, compared with the quasi-uniform distribution of the GT-repeat alleles among T235 genes; (2) the higher frequency of the T235 allele in three ethnic groups (Africans, Japanese, and Indian Americans), compared with only one group (northern Europeans) in which the M235 allele is more frequent (Jeunemaitre et al., 1992c; Hata et al., 1994; Rotimi et al., 1994; Iwai et al., 1995; Schmidt et al., 1995); and (3) the homozygosity, for T235 in 20 chimpanzees (personal results) and all primate monkeys (gorilla, orangutan, gibbon, macaque, and baboon) analyzed by Inoue et al. (1997). Thus, an accumulation of nucleotide substitutions would be more likely to happen in the T235 allele, with its longer evolutionary time span. Consequently, the primary emphasis of our inquiry was haplotypes of T235 that are derived from diallelic series.

We extensively tried to address this question by identifying new polymorphisms at the AGT locus. A total of 10 diallelic polymorphisms were genotyped in a large series of hypertensives and controls originating from two separate ethnic origins. Linkage disequilibrium observed between these polymorphisms was very similar in both Caucasians and Japanese and led invariably to a parsimonious set of five common haplotypes of T235. No special haplotype consistently accounted for this association in both groups. However, the frequencies of the two haplotypes bearing the −776 and −793 polymorphisms were found to be statistically different between hypertensive and normotensive Caucasians. These two particular haplotypes could be in linkage disequilibrium with some mutations, presently mainly in Caucasians, that would affect either the expression or the function of angiotensinogen.

Different arguments make this hypothesis unlikely. First, although not all mutations led to detectable conformation polymorphisms, only three rare mutations in the coding sequence—one at the cleavage site for renin (Inoue et al., 1995) and two others, at the 209 and 211 residues, and each detected in one African Caribbean family (Hixson et al., Powers, 1995)—have been reported so far in the literature, in comparison with our initial study (Jeunemaitre et al., 1992). Second, we could not identify any additional mutation when all exons, splice junctions, and the 3' UTR of the gene were sequenced in 16 individuals homozygous for the T235 allele. Third, substitutions at the −776 and −793 sites are not part of a theoretical consensus sequence that could play a role in angiotensinogen expression, although the case of this latter variant is more complex, since it is combined with two other substitutions (−1074 and −532). Little is known, however, about the transcriptional factors that bind to the AGT promoter, and the possibility that AGT expression may vary either because of these variants or because of other mutation(s) located farther upstream of the AGT gene cannot be ruled out. Finally, in the case of a true association, one would have to postulate that the haplotypes H3 (−776 and 235T) and H4 (—793C and 235T) do constitute different alleles predisposing to human hypertension in Caucasians but not in Japanese. Since the T235 allele was increased to the same extent in both populations, it would imply an unlikely genetic or environmental interaction specific to these haplotypes and to Caucasians.

Two reports have suggested the existence of specific alleles of the AGT gene that predispose to high BP. In their first study, involving 63 Caucasian families recruited in London, Caulfield et al. (1994) reported a surprisingly strong association between alleles of the AGT-GT repeat and essential hypertension. In particular, the most common allele in the reference population, a7 or $(GT)_{16}$, occurred at much lower frequency in the 63 hypertensive probands than in the 80 controls (0.07 vs. 0.31), whereas allele a6 or $(GT)_{17}$ exhibited the opposite trend (0.36 vs. 0.17). These results would lead to the hypothesis that two factors, one protective and the other predisposing, occur in disequilibrium with two successive alleles of the GT repeat. There are several arguments against such a complex genetic hypothesis: (1) it is not supported either by our initial study (Jeunemaitre et al., 1992c) or by the present study, each of which was performed on a much larger (greater than five-fold) number of control and hypertensive subjects; (2) the only difference in frequency of the GT alleles, observed in both Utah and Paris subjects, was a decrease in the most common allele, a7 or $(GT)_{16}$, in hypertensives compared with normotensives(0.34 vs. 0.42); (3) this difference is predicted by the linkage disequilibrium between M235 and $(GT)_{16}$ ($P[M235/(GT)_{16}]=0.92$) in those populations; and (4) the linkage disequilibrium between M235 and $(GT)_{16}$ also occurs in Japanese subjects ($P[M235/(GT)_{16}]=0.81$). The results obtained from Caulfield at al. (1994) therefore are inconsistent with the absence of a difference, in M235 frequency, between cases and controls in that particular study. The second study (Caulfield et al., 1995), which found marked differences in allele a8 and a9 frequency of the AGT-GT repeat in a limited number of African Caribbean normotensive and hypertensive subjects, would lead to the same complex genetic hypothesis.

One significant outcome of our search for a causative mutation at the AGT locus was the finding that a polymorphism occurring six residues upstream from the initiation site of transcription was in very strong linkage disequilibrium with the polymorphism at residue 235. The frequencies of the A-6 and the T235 alleles are almost identical with >97% concordance between the two substitutions, in both the French and Japanese groups. As a consequence, all statistical associations observed—and interpretations proposed—for T235 directly extend to A-6. Although the Met→Thr substitution at position 235 alters the immunological recognition of the protein (Cohen et al., 1996), expression studies do not demonstrate any difference in glycosylation, secretion, or enzymatic properties between the two recombinant angiotensinogens (Inoue et al., 1997). By contrast, the region encompassed by positions −15 and −1 of the human AGT gene represents a transcriptionally important cis-acting sequence (Yanai et al., 1996). However, the role of this region in AGT transcription could be complex, since different nuclear factors seem to bind at the 5' versus 3' parts of this cis-acting element (Yanai et al., 1996; Inoue et al., 1997). Interestingly, in vitro experiments demonstrate that the G→A substitution at position −6 affects the basal transcription rate of the AGT gene (Inoue et al., 1997). Thus, this substitution actually could represent the causative mutation explaining the association between T235 and both increased plasma angiotensinogen and, consequently, hypertension.

Until the development of genetically selected strains of animals, humans appeared to be a unique species in their apparent predisposition to hypertension, suggesting a specific interaction between genetic factors and the variation of human environment (McCarron et al., 1983). On the basis of our data, it is tempting to speculate about the role of different angiotensinogen alleles in this interaction. Through the phylogenetic history of the vertebrates, it has become clear that the renin angiotensinogen system has played a key role in the adaptation of living creatures to their salt environment, from marine to freshwater milieu, from aquatic to terrestrial life, maintaining blood pressure and sodium balance through vasoconstriction and salt retention (Henderson et al., 1993). It is very likely that, several million years ago, the diet of hominoids was almost exclusively vegetarian (Eaton et al., 1985), thus containing a very low level of sodium and a high potassium intake, which can constitute a strong selective environment. That selection pressure could have favored salt retention mechanisms already developed at earlier stages of phylogeny, resulting in the selection of alleles resulting in an optimal salt reabsorption (Denton, 1984). This environmental stressor could have been even stronger for the first ancestors of the human species, because of the change to the environment (from forest to savana) and to the required adaptation to upright posture. The angiotensinogen allele would be one of these genes leading to increased sodium reabsorption and increased blood pressure. It is interesting to note that the T235T/A-6 allele is found in chimpanzees, in which an increased salt intake causes a large rise in blood pressure (Denton et al., 1995). More recently, increased availability and use of salt may have allowed genetic variants with a lesser effect on sodium retention and on blood pressure to accumulate, resulting in the development of salt resistance. Nowadays, the analysis of different living human groups shows not only different frequencies of the T235 allele, according to their diversity and history, but also the residual effect of this gene on blood pressure in a modified environment.

EXAMPLE 10

Effect of Duplication at AGT Locus

1. Gene Disruption and Gene Duplication by Targeting.

Conventional gene targeting in embryonic stem cells derived from the mouse inbred strain 129 has been used to disrupt the AGT gene and to delete the nucleotides that encode angiotensin 1. The target gene (Clouston et al., 1988), targeting construct, and resulting chromosome are shown in Kim et al. (1995). A male chimera generated from one of the targeted embryonic stem cell colonies transmitted the disrupted AGT gene to its offspring.

A method for duplicating genes by gap-repair gene targeting and its application to the mouse AGT gene have been described elsewhere (Smithies et al., 1994), and the resulting chromosome are shown in Kim et al. (1995). The whole of the gene, including all known regulatory sequences, is tandemly duplicated at its natural chromosomal locus together with about 3 kb of DNA 5' to the start of transcription of the gene and about 200 bp 3' to the poly(A) addition site.

2. Generation of Animals Having Various Numbers of Functional AGT Genes.

Chimeric males carrying the disrupted or the duplicated AGT gene were mated with inbred strain B6 females. The resulting (129×B6) $F_1$ mice are genetically identical except for their AGT genotypes and sexes. Three AGT genotypes are possible in these $F_1$ animals: 1/0 (one normal and one disrupted copy), 1/1 (normal), and 2/1 (one duplicated and one normal copy), corresponding to one, two, and three functional copies of the AGT gene.

When suitable $F_1$ pairs are bred, three additional AGT genotypes arise in $F_2$ mice; 0/0 (both copies disrupted), 2/0 (having one chromosome with the AGT gene duplicated and one with the gene disrupted), and 2/2 (both copies duplicated). All six AGT genotypes are distinguishable at the DNA level by using Southern blots (FIG. 1C) or PCR with the probes and primers illustrated in Kim et al. (1995). However, Southern blots of DNA from 2/1 and 2/2 animals differ only in the relative intensities of autoradiographic bands, unless the diagnostic restriction enzyme sites lie outside the (18-kb) duplicated AGT gene region. It is preferred to distinguish these two genotypes by scoring for a simple sequence fragment, D8M1T56 (Copeland et al., 1993), which is closely linked to the AGT locus and which differs in length in strain B6 (160 bp) and strain 129 (182 bp). In the $F_2$ mice, the singleton AGT gene is always derived from strain B6, and the duplicated gene is always derived from strain 129. In the absence of crossovers, 2/1 and 2/2 genotypes are therefore distinguishable by PCR for the simple sequence; 2/1 animals give both the 160-bp and the 182-bp fragments; 2/2 animals give only the 182-bp fragment. Crossovers between the AGT gene and D8M1T56 will cause errors in this typing procedure. However, the frequency of such crossovers must be small, since we have observed none in approximately 90 meioses in which they would have been identified by observing absence of 129-derived fragment from animals having the duplicated gene.

To study the relative survival of pups with different numbers of functional copies of AGT, data from 39 $F_1$ matings yielding over 240 weanings is collected. The results showed no significant deviations from Mendelian expectation in the survival to weaning of pups with one, two, three, or four functional copies of the AGT gene, but there was a highly significant (P<0.001 by $X^2$) deficiency of 0/0 pups (23 expected, three observed). It was found that a high proportion of 0/0 pups among the pups that died before weaning. Therefore, a litter from a 1/0×1/0 cross was sacrificed immediately after birth, and it was found that the three possible genotypes were represented in Mendelian proportions (three were 0/0, five were 1/0, and two were 1/1). Thus, absence of a functional AGT gene is compatible with survival to birth, but postnatal survival is severely compromised.

3. Plasma AGT Concentrations vs. AGT Genotype.

Smithies et al. (1994) have reported the steady-state plasma AGT levels in (129×B6)$F_1$ animals with one, two, and three functional copies of the AGT gene. They were, respectively, 35%, 100% (by definition), and 124% that of the normal two-copy (1/1) animals. [The absolute level of AGT (±SEM) in normal $F_1$ animals is 524±0.30 nmol/ml.] The $F_2$ generation of animals allows analysis of zero-copy (0/0) and four-copy (2/2) animals. As expected, zero-copy animals (n=2) have no detectable AGT in their plasma. Four-copy animals (three males and three females) have an average AGT level of 144.5% ±4.7% of the normal two-copy (1/1, $F_1$) levels.

The $F_2$ generation also includes animals of the 2/0 genotype. These animals have a duplicated AGT locus on one chromosome 8 and a disrupted AGT gene on the other. In contrast, normal (1/1) animals have a singleton AGT gene on each parental chromosome 8. Comparisons between these two types of animal are therefore informative with respect to the function of the duplicated AGT gene. The steady-state plasma AGT levels in 2/0 $F_2$ animals (three males and three females) was found to be 55.0% ±1.5% of the normal 1/1 $F_1$ level. The AGT levels of the 1/0 $F_1$ animals are 35% of normal. Thus, the duplicated AGT locus leads to the synthesis of more AGT than does one normal singleton AGT gene, in confirmation of earlier $F_1$ studies (Smithies et al., 1994), but to less than can be achieved with two normal singleton genes.

Comment is required on the plasma AGT levels of the one-copy $F_1$ animals, which are 35% of normal, rather than the 50% level expected from a linear relationship between AGT level and gene copy number. The plasma renin levels in these animals was found to be 250% ±5% of normal (n=9). This suggests that, in these animals, a higher-than-normal proportion of plasma AGT is being converted to angiotensin I.

4. Blood Pressures vs. AGT Genotype.

Blood pressures are measured in two ways (Krege et al., 1995); indirectly by a non-invasive computerized tail-cuff system and directly by catheterization of a carotid artery. Tail-cuff pressures (23 males and 20 females) and the mean arterial pressures (22 different males) of $F_2$ animals having various numbers of functional AGT genes were examined. The overall picture is clear: blood pressures increase with increasing numbers of functional AGT genes. Several tests establish the statistical significance of these results. Regression analysis with mean arterial pressure as the dependent variable shows a highly significant effect of AGT copy number (correlation coefficient 0.60; slope 8.3±2.3 mmHg per copy; P<0.01). Regression analysis with tail-cuff blood pressure as the dependent variable also indicates a significant effect of AGT copy number (correlation coefficient 0.38; slope 3.7±1.4 mmHg per copy; P<0.02). Because the two groups of animals used in these experiments were independent, the probability of the combined results occurring by chance can be calculated from the individual probabilities as described by Fisher (70); the combined probability is 0.0005.

Inclusion in the tail-cuff group of animals of both sexes allows the use of two-factor analysis of variance to assess any effects of gender. This analysis shows that neither gender (P=0.57) nor the interaction of gender and AGT copy number (P=0.11) is significantly correlated with tail-cuff blood pressures.

The 2/0 $F_2$ animals had intra-arterial blood pressures (132±3 mmHg, n=4) that did not differ significantly (P>0.6) from the pressures of 1/1 $F_2$ animals (129±4 mmHg, n=9).

5. Exclusion of the Effects of Linked Genes.

Some, although not all, of the $F_2$ mice differ systematically only at the AGT locus. The one-copy (1/0) and three-copy (2/1) $F_2$ animals are of this category. Thus, the wild-type AGT allele plus neighboring linked genes in all the one-copy and three-copy $F_2$ animals are derived from strain B6; their other AGT allele (which differs in being disrupted or duplicated) plus neighboring linked genes are derived from strain 129. Analysis of the data from these one-copy and three-copy $F_2$ animals can therefore be used to exclude any possible effects of linked genes. (Unlinked genes segregate randomly in the $F_2$ generation and so do not differ systematically between these groups of animals.) It is found, in agreement with the results from the complete set of $F_2$ animals, that the one-copy and three-copy $F_2$ animals show the same effect of AGT gene copy numbers on blood pressures. Thus, regression analysis of the intra-arterial data from the one-copy and three-copy $F_2$ animals showed a slope of 8.1±4.0 mmHg per copy, n=10, P<0.05; similar analysis of the tail-cuff data from different one-copy and three-copy $F_2$ animals showed a slope of 7.7±2.1 mnHg per copy, n=, P <0.001. The combined probability is <0.0005. Therefore, the demonstrated effects of AGT gene copy number on blood pressure are independent of any other genetic differences linked or unlinked to the locus.

EXAMPLE 11

In Vitro Analysis of the G-6A Mutation

Promoter Assays Reveal a Significant Effect of the 6 Substitution on Basal Transcription.

In tests of the promoter of human AGT, it has been reported that deletions from −1222 to −33 did not significantly change promoter activity. By contrast, removal of the region from −16 to +44 led to sharply reduced expression of a reporter gene in HepG2 cells (Fukamizu et al., 89). In independent experiments, a ubiquitous transcription factor binding to a segment of the murine AGT promoter spanning residues −6 to +22 appeared to be a major determinant of basal transcriptional activity (Tamura et al., 1994). These reports pointed to the functional significance in gene expression of the proximal region of the AGT promoter.

Fusion genes to express the luciferase gene under control of segments of human AGT were generated. Three classes of expression vectors were constructed (Inoue et al., 1997). Vector I (−256,+90) differs from the shorter vector II (−70, ±90) by the inclusion of two putative glucocorticoid responsive elements; vector III (−256, −17) served as a control of AGT promoter expression. Vectors of classes I and II were each constructed in two forms, which differed only by the presence of either a guanine or an adenine at the −6 position. Cultured cells were transfected in parallel to evaluate the effect of this substitution on transcriptional activity. All experiments included parallel transfections of both a positive control expressing luciferase under the control of an SV40 promoter and enhancer, and a promoterless negative control. To correct for variability in transfection efficiency, every plate was cotransfected with a vector expressing chloramphenicol acetyl transferase (CAT) under the control of an SV40 promoter, and individual luciferase measurements were standardized by their corresponding CAT activities. All experiments were performed in quadruplicate.

Two different cell lines were used, the human hepatoma cell line HepG2, which expresses endogenous AGT, and the human embryonal kidney cell line 293, in which AGT mRNA could not be detected by Northern blot analysis. Because of the variability inherent to such experiments, and to achieve high statistical power to detect an effect expected to be moderate (tho-fold or less), 10 independent experiments were conducted with each cell type.

In HepG2 cells, positive controls yielded standardized activities in large excess (10- to 50-fold) of those exhibited by AGT fuision genes. In 293 cells, the activities recorded for positive controls were similar to those obtained with vector I. Negative controls were, as a rule, an order of magnitude or more below other experimental values. Vector III typically yielded values between one-half and one-third of those recorded for vector II-G. For clarity of presentation, only the data pertaining to vectors I and II are reported in the figures.

The data obtained in HepG2 cells are as follows. It is clear that the largest source of variation occurs among experiments, and that the effect of the nucleotide substitution can be better appreciated by comparing activities within experiments. This conclusion is conveyed more formally by the results of the analysis of variance, where mean squares provide estimates of variance arising from each identified source of variation. While this variance is large among experiments (1718.08), the variance as a result of the substitution effect (753.96) is much in excess of the random variability, or residual variance, among replicates (27.68). Under the hypothesis of no experiment effect and no substitution effect, these three components should provide independent estimates of the same variance. Dividing the mean squares attributed to either effect by the residual mean squares provides a test of significance of the effect, which is distributed as an F-statistic. Thus, the effect of experiment yields a ratio of 1718.08/27.68=62.07, an F-statistic with 9 and 59 degrees of freedom under the null hypothesis. This is highly significant, as the nominal value obtained by reference to the F-distribution is $<10^{-10}$. While also significant, the interaction effect is small compared to other sources of variation tested, suggesting that departures from the assumptions of the model have little impact on this statistical inference. The effect of the nucleotide substitution was highly significant (753.96/27.68=27.24, an F-statistic with 1 and 59 degrees of freedom under the null hypothesis, $P=2.4\times10^{-6}$), with A(−6) yielding expression levels 19.3% higher than G(−6). Similar results hold for vector II. Variation among experiments was quite significant ($F_{9,59}=58.11$, $P<10^{-10}$), and the interaction effect was modest ($F_{9,59}=3.48$, P=0.002). The substitution effect was quite evident ($F_{9,59}=87.26$, $P<10^{-10}$), with expression levels 36.7% higher for A(−6) than for G(−6).

In other analyses, it was verified that statistical significance did not result from the presence of extreme, outlying values. The data was also examined after standardization within experiment, as described in Inoue et al., 1997), which yielded a statistic distributed as Student's t under the null hypothesis of no substitution effect. There were 39 and 40 observations for vectors with G or A at position −6, respectively. In one analysis, the means (and SD) of the standardized activities were −0.52 (0.86) and 0.51 (0.72), respectively, yielding t=5.76 and $P=8.2\times10^{-8}$. Similarly, in analysis, the corresponding means (and SDs) were −0.72 (0.49) and 0.71 (0.71), yielding t=10.45 and $P=1.1\times10^{-16}$. Non-parametric tests were also highly significant. This overall consistency establishes the true statistical significance of the nucleotide substitution effect.

In four additional preliminary experiments conducted in HepG2 cells (data not shown), lower transfection efficiency was achieved but a significant effect of the nucleotide substitution was also noted for both classes of vectors (vector I: $F_{1,22}=14.49$, P=0.001, 47.4% higher levels observed with A than with G; vector II: $F_{1,24}=26.78$, $P=2.7\times10^{-5}$, levels 39.6% higher with A than with G). The multiple additional tests described in Inoue et al. (1997) yielded uniformly consistent, highly significant results.

The results of experiments conducted in the 293 cell line are summarized as follows (see also Inoue et al., 1997). Vector I led to no significant substitution effect ($F_{9,60}=1.14$, $P=0.29$). Experiment 8 appeared as a clear outliner, with much higher levels of expression than achieved in other experiments. When this experiment was deleted, however, various statistical tests yielded inconsistent results. The substitution effect appeared significant in the two-way analysis of variance ($F_{1,54}=15.15$, $P=0.00027$), but residual variances among combination of both factors were highly heterogenous; after correction for this effect by standardization, the substitution effect was no longer statistically significant ($t=1.06$, $P=0.22$). For the shorter vector II, by contrast, this effect was very significant ($F_{1,60}=56.25$, $P=3.5\times10^{-10}$), with A(−6) exhibiting levels of expression 68.6% than G(−6), and this was confirmed by all other analyses.

The expression levels achieved by the AGT-luciferase fusion genes were higher in the 293 cell line than in HepG2 cells, particularly for vector I. This difference was not because of a cell-specific difference in transfection efficiency, however, as the levels observed for the positive controls were actually higher in the HepG2 than in the 293 cell line.

2. The substitution Effect is Consistently Observed With Different Plasmid Preparations.

Although multiple independent plasmid preparations were used in the course of these experiments, the extent to which different plasmid isolates can affect the experimental results was specifically examined. For class II vectors with either G or A at residue −6, two different plasmid preparations were used in parallel transfection experiments in the 293 cell line. The substitution effect was again significant ($F_{1,8}=45.33$, $P=0.00015$; 48% greater expression levels with A than with G), whereas plasmid preparation was not a significant source of variation ($F_{1,8}=0.22$, $P=0.65$).

3. The Substitution Effect is not an Artifact of Prokaryotic Methylation.

The G to A substitution occurs at a site (CCAGG) recognized by the *Escherichia coli* K12 methylase dcm, and methylation of the internal cytosine may affect transcription in various ways (Volpe et al., 1993), including enhancement. This raised the possibility that the differences reported above might be an artifact of prokaryotic methylation. To test this hypothesis, vectors of both classes were propagated in the dam⁻dem⁻*E. coli* strain DM1, and the corresponding plasmid isolates were used for another series of transfection experiments. In all instances, the nucleotide substitution produced a highly significant effect on transcription, generally higher than observed with plasmid propagated in DH5α.

4. An Olizonucleotide Spanning −6 Interacts With at Least Two Distinct Protein Complexes.

That the substitution at nucleotide −6 affects the rate of transcription of AGT implies that nuclear proteins involved in either assembly or regulation of the pre-initiation complex interact with the proximal region of the AGT promoter. In gel retardation assays with nuclear extracts prepared from HepG2 cells, a 23-mer oligonucleotide centered on a G nucleotide at −6 (G23) revealed two major retarded complexes. The slower moving complex appeared to include two poorly resolved components. Competition experiments with oligonucleotides containing binding sites for a panel of transcription factors, as well as additional oligonucleotides with random composition, showed that the faster complex bound to DNA in a nonspecific fashion. By contrast, the slower complex was quantitatively reduced when amounts of homologous competitor were increased (FIG. 5.). It was also slightly reduced by the oligonucleotide harboring an Sp1 consensus binding site; however, experiments involving a radiolabeled oligonucleotide containing an Sp1 consensus binding site revealed a complex of distinct mobility for which G23 exhibited no competition. Pre-incubation of nuclear extracts with increasing amounts of non-specific competitor (whether poly-(dI-dC) or is Oct-1 recognition site) led to a marked reduction in the intensity of the faster complex, although it was not possible to totally compete away this complex and still retain the slower, specific component. Binding by the latter was observed with nuclear extracts from all human cells tested except HeLa.

5. The Nonspecific Complex Corresponds to Human Ku Antigen.

In an attempt to identify the proteins responsible for the observed DNA binding activities, nuclear extracts prepared from a 2-1 suspension culture of MOLT4 cells were subjected to QAE sepharose and DNA affinity chromatography. From this preparation, only the nonspecific binding activity could be identified in eluted fractions. Two polypeptides with apparent molecular mass of 70 and 86 kD on denaturing gels were subjected to digestion with endoprotease Lys-C followed by microsequencing. The sequence of two peptide fragments of the 86 kD protein (IEIFTDLSSRF (SEQ ID NO:54) and KTDTLEDLFP (SEQ ID NO:55)) was identical to the p86 component of the heterodimeric human Ku nuclear antigen (Mimori et al., 1986); similarly, fragments of the 70 kD component consisted of sequences (LYRETNEPVK (SEQ ID NO:56), TRTFNT (SEQ ID NO:57), IMATPEQVGK (SEQ ID NO:58)) found in the p70 component of Ku antigen (Reeves et al., 1989). It is generally recognized that the Ku heterodimer binds to DNA ends with no apparent sequence specificity (Mimori et al., 1986). Consequently, all subsequent binding experiments included a 100-fold molar excess of the Oct-1 oligonucleotide as an additional nonspecific competitor.

6. Competitive Binding Studies Suggest that the Nucleotide Substitution Affects the Binding Affinity of the Specific Complex.

Having confirmed the lack of specificity of the faster complex, the binding behavior of the slower complex was examined, in search of differences in affinity which could account for the effect of the nucleotide substitution observed in promoter assays. In direct binding experiments involving the G23 and A23 oligonucleotides, A23 appeared to retard only the faster moving component of this complex. Competition studies involving G23 radiolabeled oligonucleotide revealed quantitative reduction of both components of the slow moving complex with increasing concentrations of G23 cold competitor. By contrast, only the faster component was reduced when A23 was used as competitor. These patterns were reproducible in several independent experiments.

7. Mutational Studies Confirm the Significance of the −6 Region in Transcriptional Activity Both the promoter expression and the competitive binding experiments suggested that a transacting factor binds specifically to the proximal promoter of AGT to modulate its expression, and that the affinity of this site is affected by the nucleotide substitution at position −6. It was not possible to characterize this binding site further either by DNaseI footprinting or by methylation interference using total nuclear extracts from HepG2 cells, as these experiments revealed no specific protection or contacts.

Systematic mutagenesis was used as an alternative. Oligonucleotides with substitutions scanning the proximal promoter of AGT from nucleotides −13 to +2 were synthesized and used in gel retardation assays. Direct binding studies suggested differences in the affinity of the mutant oligonucleotides for either component of the specific complex, and this was further supported by the reciprocal patterns observed when such mutant probes were used as cold competitors. These data provide additional evidence in support of the interpretation that the specific complex consists of at least two unresolved components.

Mutations M2, M3, and M4 (Inoue et al., 1997) were introduced in expression vectors of classes I and II by oligonucleotide-directed mutagenesis and used in promoter assays in both the HepG2 and the 293 cell lines. For each cell type three experiments were performed, each with five experimental vectors, a positive control, and a negative control. All transfections were performed in triplicate. The analysis of the data required the consideration of two factors, experiment and vector, with three and five modalities, respectively. In all instances the overall effects of both factors were highly significant: the F-statistic testing the effect of the vectors, with 4 and 30 degrees of freedom, ranged from 64.09–404.39. This provided confirmation that alterations of the sequence in this region directly affect transcriptional activity in these experiments. The effects of particular substitutions were examined by contrasting the standardized luciferase activities observed for each vector to that observed for the reference vector with a guanine at site −6, yielding statistics distributed as Student's t under the null hypothesis. A consistent picture arose from these four sets of experiments, with similar statistical significance when analyses were performed after standardization within an experiment. Higher expression levels were consistently observed for A(−6) and mutants M3 and M4 than for G(−6). By contrast, mutant M2 had the opposite effect. These data confirmed the inference arising from our previous experiments, namely that variation in expression and affinity associated with the nucleotide substitution at position −6 appears to result from the specific binding of a trans-acting factor which has the net effect of decreasing transcriptional activity in the vector carrying G rather than A at position −6. They also suggested the net stimulating effect of another factor binding to the region altered by M2.

8. The Transcriptional Difference Detected May Have an Impact on Physiological Function.

The statistical significance achieved in the initial series of promoter assays and the replication afforded by subsequent experiments testing the effects of independent plasmid isolates, of plasmid propagation in the DM1 prokaryotic host, or of mutations in this region of the 4GT promoter all support the conclusion that the nucleotide substitution affects basal transcription in these assays. The question, then, is whether a moderate difference in basal transcriptional activity, ranging from 20 to 70%, could be of physiological consequence ini vivo and contribute to the development of essential hypertension.

It is clearly not possible to directly extend the results of transfection experiments done with truncated AGT promoters in cultured cells to the function of an intact AGT gene at the level of the whole organism. Manipulation of the number of AGT genes in the mouse by targeted gene duplication has provided direct evidence that a modest increase in gene expression leads to elevated plasma angiotensinogen and a significant rise in blood pressure (Smithies et al., 1994; Kim et al., 1995). Recent observations provide a direct in vivo correlation for ice vitro observations; in total RNA prepared from decidual specimen collected from 39 women who under-vent first-trimester elective abortion and were heterozygous at residue 235, T235 was significantly in excess over M235, suggesting a difference in transcriptional activity between the two forms of the AGT gene. Although the correlations noted cannot establish proof of causal relationships, these data support the contention that a modest difference in transcriptional activity, as noted ini vitro for variant A(−6), could be of physiological consequence and contribute to the development of essential hypertension 9. Preferential Binding of a Trans-acting Factor to G(−6) Leads to a Net Reduction in Transcriptional Activity.

The slower-moving complex in gel retardation experiments appeared to be specific, as it could be competed away effectively only by homologous oligonucleotides. Further binding studies suggested that this complex consisted of two distinct components, with higher affinity of the upper component of the complex for AGT oligonucleotides which have G rather than A at position −6. The lower levels of expression observed with G instead of A in the transactivation experiment suggested a net reduction in transcriptional activity as a result of an interaction with this upper component. Binding experiments involving G23 and mutant oligonucleotides revealed subtle but reproducible differences in electrophoretic mobility of the slower-moving complex, particularly for mutants M3 and M4, which further documented the heterogeneity of this complex. Transactivation experiments confirmed the interaction of a factor leading to reduced promoter activity at a site spanning nucleotide −6 and extending in the 3' direction, the segment probed by mutants M3 and M4. They also suggested that an activator may bind to an overlapping site extending in the 5' direction. While there is published evidence (Tamura et al., 1994) for the interaction of an activator in segment −6 to +22 of the murine AGT promoter when expressed in human HepG2 cells, this site was mapped by mutagenesis downstream from the initiation site of transcription. Evidence for another activator. binding to segment −26 to −9 of the proximal promoter of human AGT was reported recently (Yanai et al., 1996); in binding and competition experiments, differences in electrophoretic mobilities and lack of reciprocal cross-competition support the interpretation that the factors interacting at the site centered on nucleotide −6 are distinct from those at this more distal site.

EXAMPLE 12

In Vitro Analysis of the A-20/C Mutations

In studies similar to those described in Example 11, binding experiments involving DNA segments spanning the −20 and −6 sites were performed. It was found that two transcription factors, the Upstream Stability Factor (USF) and the estrogen receptor (ER), bound to this DNA segment. It was further found that the polymorphism at the −20 site affected the affinity of these factors for this segment of the AGT promoter. It was found that A(−20) modulates the effect of A(−6). That is, the two transcription factors studied have a lower affinity for A(−20)/A(−6) than C(−20)/A(−6). While the AGT promoter with A(−6) has higher transcriptional activity, this effect can be affected by the base at the −20 position. If the base at the −20 position is the native C, the increased transcriptional activity is modulated, i.e., reduced, when compared to an A at the −20 position. As seen above in Examples 10 and 11, the in vitro activity of the AGT promoter correlates and is predictive of the in vivo activity of the promoter.

In view of these in vitro and in vivo studies, and the data presented in Examples 1–9, it is clear that it has been established that the G-6A mutation predisposes to hypertension, and particularly salt-induced hypertension. The binding experiments of the present Example also demonstrate that an analysis of the −20 site should be performed, and that such an analysis is useful for determining the prognosis of the hypertension. That is, an analysis of the −20 site is useful in determining the potential severity of the hypertension in individuals which are predisposed to hypertension as a result of the G-6A mutation. The prognosis is determined by analyzing the DNA of an individual at the −20 and −6 sites. The finding of an A instead of a G at the −6 site indicates a predisposition to hypertension. The finding of an A at the −20 site indicates that the potential severity of hypertension resulting from the 6–6A mutation is lower than if a C is found at the −20 site. The individual with A(−20) remains at risk for hypertension, while the individual with C(−20) has a risk for more severe hypertension or has a higher risk for hypertension.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Amal, J. F., et al. (1991). *Am. J. Med.* 90:17–22.
Alhenc-Gelas, F., et al. (1991). *J. Lab. Clin. Med.* 117:33–39.
Bachmann, J., et al. (1991). *J. Steroid Bioclein. Mol. Biol*: 40:511–515.
Blackwelder, W. C. and Elston, R. C. (1985). *Genet. Epiderniol.* 2:85–97.
Bishop, D. T. and Williamson, J. A. (1990). *Am. J. Hum. Genet.* 46:254–265.
Bratusch-Marrain, P. R. et al. (1982). *J. Clin. Endocrinol. Met.* 55:973–982.
Brown, A. J., et al. (1981). *Am. J. Physiol*: 241:H381–H388.
Cain, M. D., et al. (1971). *J. Clin. Endocrinol.* 33:671–676.
Campbell, D. J., and Habener, J. F. (1986). *J. Clin. Invest.* 78:1427–1431.
Carrell, R. W., and Boswell, D. R. (1986). In: *Proteinase Inhibitors*, Barrett and Salvesen, eds., (Elsevier Science Publishers BV, Biomedical Division), pp. 403–420.
Cariello (1988). *Human Genetics* 42:726.
Caulfield, M., et al. (1994). *N. Eng. J. Med.* 330:1629–1633.
Charru, A., et al. (1994). *J. Hyper-Tens.* 12:981–985.
Chen, E. Y., et al. (1989). *Genomics* 4:479–487.
Clauser, E., et al. (1989). *Am. J. Hypertens.* 2:403–410.
Clouston, W. M., et al. (1988). *Genomics* 2:240–248.
Cohen, P. et al. (1996). *J. Clin. Endo. Metab.* 81:3505–3512.
Conner, B. J., et al. (1983). *Proc. Natl. Acad. Sci. USA*. 80:278–282.
Copeland, N. G., et al. (1993). *Science* 262:57–66.
Corvol, P., et al. (1989). *Clin. Exper. Hypertension: Theory & Practice.* A11:1053–1073.
Cotton, et al. (1988). *Proc. Natl. Acad. Sci. USA* 85:4397.
Cudworth, A. G., and Woodrow, J. C. (1975). *Brit. Med. J.* 111:133–135.
Dausset, J., et al. (1990). *Genomics* 6:575–577.
Deng, Y., and Rapp, J. P. (1992). *Nature Genetics* 1:267 272.
Denton, D., et al. (1984). In: *The Hunger for Salt: An Anthzropological, Physiological and Medical Analysis*, Springer, N.Y., pp. 53–75.
Denton, D., et al. (1995). *Nat. Med.* 1:1009–1016.
Eaton, S. B., et al. (1985). *N. Engl. J. Med.* 312:283–289.

Fasola, A. F., et al. (1968). *J. Appl. Physiol.* 25:410–415.
Feinberg, A. P., et al. (1983). *Anal. Biochem.* 132:6–13.
Ferrami, E., et al. (1987). *N. Engl. J. Med.* 317:350–357.
Finkelstein, J., et al. (1990). *Genomics* 7:167–172.
Fisher, R. A., et al. (1970). *Statistical Methods for Research Workers*, Hafner, Darien, Conn.
Froguel, P., et al. (1992). (1992). *Nature* 356:162–164.
Froussard, P. M., et al. (I986a). *Nucl. Acids Res.* 14:6778.
Froussard, P. M., et al. (1986b). *Nucl. Acids Res.* 14:4380.
Fukamizu, A., et al. (1989). *J. Biol. Chem.* 265:7576–7582.
Gaillard, I., et al. (1989). *DNA* 8:87–99.
Gardes, J., et al. (1982). *Hypertension* 4:185–189.
Goldstein, J. L., et al. (1979). *Ann. Rev. Genet.* 13:259–289.
Gould, A. B., et al. (1971). *Cardiovasc. Res.* 5:86–89.
Hall, J. E., and Guyton, A. C. (1990). In: *Hypertension: Pathoplzysiology Diagniosis and Management*, Laragh, J. H. and Brenner, B. M., eds., (Raven Press, Ltd., N.Y.), pp. 1105–1129.
Hamilton, M., et al. (1954). *Clin. Sci.* 13:273 304.
Harper, M. E., et al. (1982). *Am. J. Hum. Genet.* 34:227–234.
Harrop, S. H., et al. (1990). *Hypertension* 16:603–614.
Hata, A., et al. (1990). *Nucl Acids Res.* 18:5407–5411.
Hata, A., et al. (1994). *J. Clin. Invest.* 93: 1285–1287.
Henderson, I. W., et al. (1993). In: *The Renin Angiotensin System*, Vol. 1 (Robertson, I. S. and Nicholls, M. G. (eds.), Gower Medical, London; N.Y.; pp. 1:2.1–2.28
Hilbert, P., et al. (1991). *Nature* 353:521–528.
Hixson, J. E., et al. (1995). *Hum. Genet.* 96:110–112.
Hill, W. G. (1975). *Biometrics* 31:881–888.
Hodge, S. E. (1984). *Genet. Epidemiol.* 1:109–122.
Hyer, R. N., et al. (1991). *Am. J. Hum. Genet.* 48:243–257.
Inoue, I., et al. (1995). *J. Biol Chem.* 270:11430–11436.
Inoue, I., et al. (1997). *J. Clin. Invest.* 99:1786–1797.
Iwai, N., et al. (1995). *Hypertension* 25(pt2):688–693.
Jacob, H. J., et al. (1991). *Cell* 67:213–224.
Jeunemaitre, X., et al. (1992a). *Nature Genetics* 1:72 75.
Jeunemaitre, X., et al. (1992b). *Hum. Genet.* 88:301–306.
Jeunemaitre, X., et al. (1992c). *Cell* 71:169–178.
Jeunemaitre, X., et al. (1997). *Am J. Hun. Geizet.* 60:1448–1460.
Joint National Committee on Detection, Evaluation and Treatment of Hypertension (1985). Final report of the Subcommittee on Definition and Prevalence Hypertension 7:457–468.
Kim, H.-S., et al. (1995). *Proc. Natl. Acad. Sci. USA* 92:2735–2739.
Kimura, S., et al. (1992). *EMBO J.* 11:821 827.
Kinszler, K. W., et al. (1991). *Science* 251:1366–1370.
Kotelevtsev, Y. V., et al. (1991). *Nucl. Acids Res.* 19:6978.
Krege, J. H., et al. (1995). *Hypertension* 25:1111–1115.
Kunapull, S. P., and Kumar, A. (1986). *Nucl. Acids Res.* 14:7509.
Kurtz, T. W., et al. (1990). *J. Clin. Invest.* 85:1328–1332.
Lalouel, J. M. (1990). In: *Drugs Affecting Lipid Metabolism*, A. M. Gotto and L. C. Smith (eds.), Elsevier Science Publishers, Amsterdam, pp. 11–21.
Lander, E. S., and Botstein, D. (1986). *Cold Spring Harbor Symp. Quant. Biol.* 51:46–61.
Lander, E. S., and Botstein, D. (1989). *Genetics* 121:185 199. Lange, K. (1986). *Am. J. Hum. Genet.* 50:283–290.
Lathrop, G. M., and Lalouel, J. M. (1991). In: *Handbook of Statistics*, Vol. 8 (Elsevier Science Publishers, Amsterdam), pp. 81–123.
Lathrop, G. M., et al. (1984). *Proc. Natl. Acad. Sci. USA* 81:8443–3446.
Lifton, R. P., et al. (1992). *Nature* 355:262–265.
Masharani, U. (1989). *Nucl. Acids Res.* 17:467

Mattei, M. G., et al. (1989). *Cytogenet. Cell Genet.* 51:1041.
McCarron, D. A., et al. (1983). *Ann. Intern. Med.* 0.98:715–719.
Menard, J., and Catt, K. J. (1973). *Endocrinology* 92:1382–1388.
Menard, J., et al. (1991). *Hypertension* 18:705–706.
Miori, T., et al. (1986). *J. Biol Chem.* 261:10375–10379.
Modrich, P. (1991). *Ann. Rev. Genet.* 25:229–253.
Motro, U. and Thomson, G. (1985). *Genetics* 110:525–538.
Mullins, J. J., et al. (1990). *Nature* 34:541–544.
Nakamura, Y. et al. (1988). *Genomics* 2:302–309.
Newton, C. R., et al. (1989). *Nucl. Acids Res.* 17:2503–2516.
Nibu, Y., et al. (1994a). *J. Biol Chem.* 269:28598–28605.
Nibu, Y., et al. (1994b). *Biochem. Biophys. Res. Commun.* 205:1102–1108.
Noftilan, A. J., et al. (1989). *Hypertension* 14:614618.
Novack, et al. (1986). *Proc. Nat. Acad. Sci. USA* 83:586.
Ohkubo, H., et al. (1990). *Proc. Nat. Acad. Sci. USA* 87:5153–5157.
Orita, M., et al. (1989). *Proc. Nat. Acad. Sci. USA* 86:2766–2770.
Plouin, P. F., et al. (1989). *Presse Med.* 18:917 921.
Pollare, T. et al. (1990). *Metabolism* 39:167–174.
Polymeropoulous, M. H., et al. (1991). *Nucl. Acids Res.* 19:689–745
Pratt, R. E., et al. (1989). *Am. J. Physiol.* 256:F469–F474.
Ptacek, L. J., et al. (1991). *Am. J. Hum. Genet.* 49:378–382.
Rapp, J. P., et al. (1989). *Science* 243:542–544.
Reaven, G. M. and Cheng, H. (1991). *Am. J. Hypertens.* 0.4:34–38.
Reeves, W. H., et al., (1989). *J. Bio. Chem.* 264:5047–5052.
Riget, B., et al. (1990). *J. Clin. Invest.* 86:1343–1346.
Riget, B., et al. (1992). *Nucl. Acids Res.* in press.
Risch, N. (1990). *Am. J. Hum. Genet.* 46:242–253.
Rotitni, C., et al. (1994). *Hypertension* 24:591–594.
Ruano & Kidd (1989). *Nucl Acids Res.* 17:8392.
Rust, S., et al. (1993). *Nucl. Acids Res.* 21:3623–3629.
Sassaho, P., et al. (1987). *Am. J. Med.* 83:227–235.
Schmidt, S., et al. (1995). *Nephrol. Dial. Transplant* 10:1145–1148.
Sealey, J. E., and Laragh, J. H. (1990). In: *Hypertension: Pathophlysiology. Diagnlosis and Management*, J. H. Laragh and B. M. Brenner, eds. (Raven Press, New York), pp. 1287–1317.
Sheffield, V. C., et al. (1989). *Proc. Nat. Acad. Sci. USA* 86: 232–236.
Shenk, et al. (1975). *Proc. Nat. Acad. Sci. USA* 72:989.
Smithies, O., et al. (1994). *Proc. Nat. Acad. Sci. USA* 91:3612–2615.
Soubrier, F., et al. (1986). *Gene* 41:85–92.
Soubrier, F. (1990). *Hypertension* 16:712 717.
Stalling, R. L., et al. (1991). *Genomics* 10:807–815.
Suarez, B. K., et al. (1978). *Ann. Hum. Genet.* 42:87–94.
Suarez, B. K. et al. (1983). *Ann. Hum. Genet.* 47:153–159.
Suarez, B. K., and Van Eerdewegh, P. (1984). *Am. J. Med. Genet.* 18:135 146.
Tamura, K., et al. (1994). *J. Clin. Invest.* 93:1370–1379.
Tewksbury, D. A. (1990). In: *Hypertension: Pathophzysiology, Diagnosis and Management*, Laragh, J. H. and Brenner, B. M., eds., (Raven Press, Ltd., New York), pp. 1197–1216.
Volpe, P., et al., (1993). *FEBS Lett.* 329:233–237.
Walker, W. G., et al. (1979). *Hypertension* 1:287 291.
Ward, R. (1990). In: *Hypertension: Pathophysiology. Diagnosis and Management*, Laragh, J. H. and Brenner, B. M., eds., (Raven Press, Ltd., New York), pp. 81–100.
Wartell, R. M., et al. (1990). *Nucl. Acids Res.* 18:2699–2705.
Watt, G. C. M., et al. (1992). *J. Hypertens.* 10:473–482.
White, R. L., and Lalouel, J. M. (1987). In: *Advances in Human Genetics*, Vol. 16, H. Harris and K. Hirschhorn, eds. (Plenum Press, New York), pp. 121–228.
Williams, R. R., et al. (1988). *J. Am. Med. Assn.* 259:3579–3586.
Williams, R. R. (1989). *Hypertension* 14:610–613.
Yanai, K. Y., et al. (1996). *J. Biol. Chem.* 271:15981–15986
Yongue, B. G., et al. (1991). *Hypertension* 17:485–491.
Published European Patent No. 0332435.

---

What is claimed is:

1. A method for determining the prognosis of a predisposition of a human to hypertension, wherein said human has a predisposition to hypertension at the angiotensinogen (AGY) gene as determined by a polymorphism or mutation in the AGT gene, which comprises analyzing the DNA sequence of the AGT gene of said human for the mutation A-20C, whereby the presence of said mutation in a human having a predisposition to hypertension is indicative of either a greater predisposition of said human to hypertension or a predisposition of said human to a more severe hypertension compared to a human having a predisposition to hypertension based on the same polymorphism or mutation but who does not have the A-20C mutation.

2. The method of claim 1 wherein a genomic sequence of the AGT gene of said human is analyzed.

3. The method of claim 1 wherein a cDNA sequence of the AGT gene of said human is analyzed.

4. The method of claim 1 wherein a part of a genomic sequence of the AGT gene of said human is analyzed.

5. The method of claim 1 wherein a part of a cDNA sequence of the AGT gene of said human is analyzed.

6. The method of claim 1 wherein said analysis is carried out by hybridization.

7. The method of claim 6 wherein said hybridization is with an allele-specific oligonucleotide probe.

8. The method of claim 1 wherein said analysis is carried out by sequence analysis.

9. The method of claim 1 wherein said analysis is carried out by SSCP analysis.

10. A method for determining a prognosis of a predisposition of a human to hypertension, which comprises analyzing the DNA sequence of the AGT gene of said human for (a) either the mutation G-6A or the mutation M235T, and (b) the mutation A-20C, whereby (i) the presence of the mutation G-6A or the mutation M235T and the absence of the mutation A-20 is indicative of a predisposition of said human to hypertension, and (ii) the presence of the mutation G-6A or the mutation M235T and the presence of the mutation A-20C is indicative of either a greater predisposition of said human to hypertension or a predisposition of said human to a more severe hypertension.

11. The method of claim 10 wherein a genomic sequence of the AGT gene of said human is analyzed.

12. The method of claim 10 wherein a cDNA sequence of the AGT gene of said human is analyzed.

13. The method of claim 10 wherein a part of a genomic sequence of the AGT gene of said human is analyzed.

14. The method of claim 10 wherein a part of a cDNA sequence of the AGT gene of said human is analyzed.

15. The method of claim 10 wherein said analysis is carried out by hybridization.

16. The method of claim 15 wherein said hybridization is with allele-specific oligonucleotide probes.

17. The method of claim 10 wherein said analysis is carried out by sequence analysis.

18. The method of claim 10 wherein said analysis is carried out by SSCP analysis.

* * * * *